United States Patent [19]

Fuse et al.

[11] Patent Number: 5,294,643
[45] Date of Patent: Mar. 15, 1994

[54] CINNAMAMIDE DERIVATIVE

[75] Inventors: Yoshihide Fuse; Kenji Fujii, both of Takasago; Keiji Kameyama, Mihara; Taizo Kawabe, Takasago; Toshiaki Miwa; Ikuo Katsumi, both of Kobe, all of Japan

[73] Assignee: Kanegafuchi Kagaku Kogyo Kabushiki, Osaka, Japan

[21] Appl. No.: 548,121

[22] Filed: Jul. 5, 1990

[30] Foreign Application Priority Data

| Jul. 5, 1989 | [JP] | Japan | 1-174820 |
| Jul. 5, 1989 | [JP] | Japan | 1-174821 |
| Jul. 5, 1989 | [JP] | Japan | 1-174822 |
| Jan. 18, 1990 | [JP] | Japan | 2-9528 |
| Jan. 18, 1990 | [JP] | Japan | 2-9529 |
| Jan. 18, 1990 | [JP] | Japan | 2-9530 |

[51] Int. Cl.$^5$ .................. A61K 31/165; C07C 233/11
[52] U.S. Cl. .................. 514/622; 514/471; 514/521; 514/538; 514/562; 514/563; 514/615; 514/616; 558/393; 549/321; 560/39; 560/45; 562/426; 562/444; 564/150; 564/158; 564/170
[58] Field of Search .................. 564/170, 150, 158; 514/622, 471, 521, 538, 562, 563, 615, 616; 549/321; 558/393; 560/39, 45; 562/426, 444

[56] References Cited

U.S. PATENT DOCUMENTS 4,616,086  10/1986  Witte et al. .................. 544/389

FOREIGN PATENT DOCUMENTS 76996  10/1982  European Pat. Off.

OTHER PUBLICATIONS

"Studies on Styrene Derivatives. II. Synthesis and Anti-Inflammatory Activity of 3,5-Di-Tert-Butyl-4-Hydroxystyrenes", Ikuo Katsumi, et al., Chemical and Pharmaceutical Bulletin, vol. 34, No. 4, (Apr. 1, 1986), Tokyo JP, pp. 1619-1627.

"3,5-Di-Tert-Butyl-4-Hydroyxcinnamamide Derivatives as Cardiotonics and Their Preparation", Fuse Yoshihide, et al., Chemical Abstracts, vol. 110 No. 1, (Jan. 2, 1989), p. 719; col. 1; ref. No. 7874M, Columbus, Ohio, USA.

"Preparation of 3,5-Di-Tert-Butyl-4-Hydroxycinnamamide Derivatives as Antinflammatory", Ooe Takanori, et al., Chemical Abstracts, vol. 109, No. 21, (Nov. 21, 1988), p. 675; col. 1; Ref. No. 190042E, Columbus, Ohio USA.

"3,5-Di-Tert-Butyl-4-Hydroxycinnamamide Derivatives Containing Heterocycles", Chemical Abstracts, vol. 105, No. 13, (Sep. 29, 1986), p. 682; col. 2; Ref. No. 115081F, Columbus, Ohio, USA.

"Preparation of Quinolin-2-One Derivatives as Psychotropics, Antihypertensives, Antiiflammatories", Chemical Abstracts, vol. 111, No. 13, (Sep. 25, 1989), p. 651; col. 2; ref. No. 115059D, Columbus, Ohio, USA.

*Primary Examiner*—Bernard Dentz
*Attorney, Agent, or Firm*—Fay, Sharpe, Beall, Fagan, Minnich & McKee

[57] ABSTRACT

Novel cinnamamide derivatives and the salts thereof are provided. An antihyperlipidemic composition is also provided. The composition comprises an active ingredient which is at least one selected from the group consisting of the above-mentioned cinnamamide derivative and the pharmaceutically acceptable salt thereof.

2 Claims, No Drawings

CINNAMAMIDE DERIVATIVE

BACKGROUND OF THE INVENTION

1. Field of the invention:

The present invention relates to a cinnamamide derivative and the salts thereof, which are novel compounds possessing antihyperlipidemic activities in addition to being useful as intermediates for many other organic compounds; and an antihyperlipidemic composition or antiarteriosclerotic composition comprising the aforementioned substance as an active ingredient.

2. Description of the prior art:

Arteriosclerosis is one of the most widespread human diseases at the present time, and it is known that arteriosclerosis is one of the main contributing factors in angina pectoris, myocardial infarction, cerebral infarction and many other grave disorders. One of the principal causative factors of arteriosclerosis is hyperlipidemia.

As is well known, serum lipid concentrations, particularly serum cholesterol levels, are very closely related with the occurrence of arteriosclerosis. Serum cholesterol is classified into categories such as LDL (i.e., low density lipoprotein) and HDL (i.e., high density lipoprotein). The presence of LDL-cholesterol promotes the deposition of cholesterol onto the arterial walls, however, HDL-cholesterol transports excess cholesterol from the peripheral blood vessels and returns this cholesterol to the liver, thereby preventing the deposition of cholesterol onto the arterial walls. Thus, the susceptibility of the arterial walls to the accumulation of cholesterol is governed by the total serum cholesterol concentration and by the ratio of LDL to HDL. Therefore, an antihyperlipidemic agent which serves to reduce serum cholesterol levels, particularly LDL-cholesterol levels, is an important desideratum in the medical field.

In general, in many cases antihyperlipidemic agents are administered over a prolonged period, and are therefore required to be of high safety. However, existing drugs in this category, for example, clofibrate, entail serious side effects such as liver damage, therefore, they are not adequately safe.

SUMMARY OF THE INVENTION

The cinnamamide derivative of this invention, which overcomes the above-discussed and numerous other disadvantages and deficiencies of the prior art, is of the formula I:

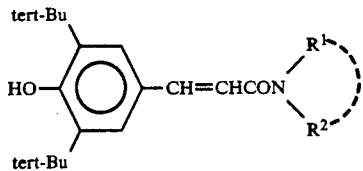
(I)

wherein $R^1$ is selected from the group consisting of hydrogen;
alkyl containing 1 to 8 carbon atoms;

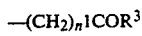

wherein $R^3$ is —OH, —OR$^4$ (R$^4$ is alkyl containing 1 to 3 carbon atoms), —NHR$^5$ (R$^5$ is alkyl containing 1 to 3 carbon atoms), —NH(CH$_2$)$_{n2}$—C$_6$H$_5$ (n$^2$ is an integer of 0 to 3),

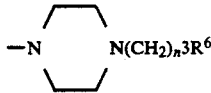

(R$^6$ is pyridyl or phenyl, and n$^3$ is an integer of 0 to 3),

(R$^7$ is alkyl containing 1 to 5 carbon atoms), or —NHNH—C$_6$H$_5$, n$^1$ is an integer of 1 to 3;

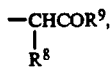

wherein $R^8$ is alkyl containing 1 to 5 carbon atoms, —(CH$_2$)$_{n4}$COOR$^{10}$ (R$^{10}$ is hydrogen or alkyl containing 1 to 3 carbon atoms, and n$^4$ is an integer of 1 to 3), —(CH$_2$)$_{n5}$OH (n$^5$ is an integer of 1 to 3), phenyl or hydroxyphenyl, and R$^9$ is —OH, —OR$^{11}$ (R$^{11}$ is alkyl containing 1 to 3 carbon atoms), or

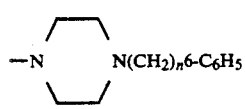

(n$^6$ is an integer of 1 to 3);

—(CH$_2$)$_{n7}$OR$^{12}$, wherein $R^{12}$ is hydrogen, alkyl containing 1 to 3 carbon atoms, —CPNHR$^{13}$ (R$^{13}$ is alkyl containing 1 to 5 carbon atoms), or —COR$^{14}$ (R$^{14}$ is phenyl, halogen-substituted phenyl, or pyridyl), and n$^7$ is an integer of 1 to 3;

—(CH$_2$)$_{n8}$SR$^{15}$, wherein $R^{15}$ is hydrogen,

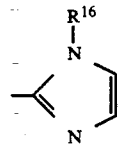

(R$^{16}$ is alkyl containing 1 to 3 carbon atoms), —(CH$_2$)$_{n9}$COOR$^{17}$ (R$^{17}$ is alkyl containing 1 to 3 carbon atoms and n$^9$ is an integer of 0 to 3),

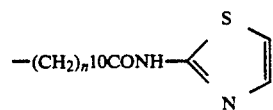

(n$^{10}$ is an integer of 0 to 3), or —(CH$_2$)$_{n11}$R$^{18}$ (R$^{18}$ is phenyl, pyridyl, pyrimidyl or benzimidazolyl, and n$^{11}$ is an integer of 0 to 3), and n$^8$ is an integer of 1 to 3;

—(CH$_2$)$_{n12}$NHR$^{19}$ wherein R$^{19}$ is

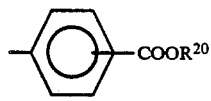

(R$^{20}$ is hydrogen or alkyl containing 1 to 3 carbon atoms), or —COR$^{21}$ (R$^{21}$ is pyridyl), and n$^{12}$ is an integer of 1 to 3;

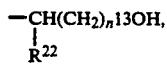

wherein R$^{22}$ is phenyl, hydroxyphenyl, and n$^{13}$ is an integer of 1 to 3;

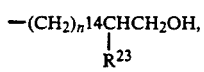

wherein R$^{23}$ is —OH or phenyl, and n$^{14}$ is an integer of 1 to 3;

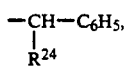

wherein R$^{24}$ is alkyl containing 1 to 3 carbon atoms, phenyl, or —CN;

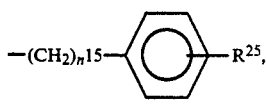

wherein R$^{25}$ is

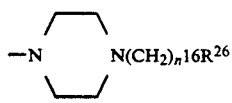

(R$^{26}$ is phenyl or pyridyl, n$^{16}$ is an integer of 1 to 3), —CONH(CH$_2$)$_{n17}$R$^{27}$ (R$^{27}$ is pyrrolidinyl substituted by alkyl containing 1 to 3 carbon atoms, or thiazolyl, and n$^{17}$ is an integer of 0 to 3), or

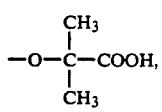

and n$^{15}$ is an integer of 0 to 3;

—(CH$_2$)$_{n18}$R$^{28}$, wherein R$^{28}$ is —CN, imidazolyl, thienyl, thienyl substituted by alkyl containing 1 to 3 carbon atoms,

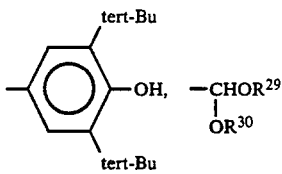

(R$^{29}$ and R$^{30}$ are independently alkyl containing 1 to 3 carbon atoms), pyridyl,

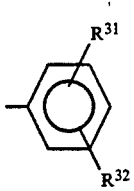

[R$^{31}$ is hydrogen, halogen, —NO$_2$, —COOH, —COOR$^{33}$ (R$^{33}$ is alkyl containing 1 to 3 carbon atoms), or —OR$^{34}$ (R$^{34}$ is alkyl containing 1 to 3 carbon atoms), and R$^{32}$ is hydrogen or —OR$^{35}$ (R$^{35}$ is alkyl containing 1 to 3 carbon atoms)],

(R$^{36}$ and R$^{37}$ are independently alkyl containing 1 to 3 carbon atoms), indolyl, or

(R$^{38}$ is pyridyl), and n$^{18}$ is an integer of 0 to 3;

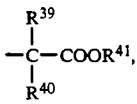

wherein R$^{39}$, R$^{40}$ and R$^{41}$ are independently alkyl containing 1 to 3 carbon atoms;

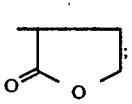

naphthyl;
indanyl;
tetralinyl; and
—COR$^{42}$, wherein R$^{42}$ is alkyl containing 1 to 3 carbon atoms; and R$^2$ is selected from the group consisting of hydrogen, alkyl containing 1 to 5 carbon atoms, and —(CH$_2$)$_{n19}$—C$_6$H$_5$ (n$^{19}$ is an integer of 1 to 3); or R$^1$ and R$^2$ may be linked together with the amide nitrogen to form a ring of

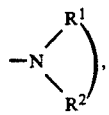

which is selected from the group consisting of

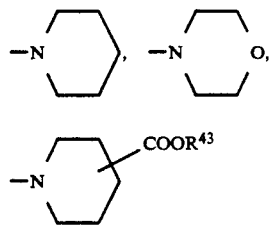

$R^{43}$ is hydrogen or alkyl containing 1 to 3 carbon atoms),

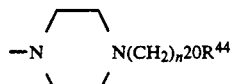

($R^{44}$ is phenyl or pyridyl, and n is an integer of 0 to 2),

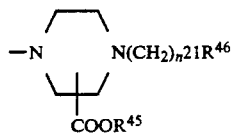

($R^{45}$ is hydrogen or alkyl containing 1 to 3 carbon atoms, $R^{46}$ is phenyl or pyridyl, and $n^{21}$ is an integer of 0 to 2), and

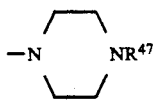

($R^{47}$ is alkyl containing 1 to 5 carbon atoms).

This invention also includes salts of the said cinnamamide derivative. An antihyperlipidemic composition of this invention comprises an active ingredient which is at least one selected from the group consisting of the above-mentioned cinnamamide derivative and the pharmaceutically acceptable salt thereof.

Thus, the invention described herein makes possible the objectives of:

(1) providing a novel compound that possesses the functions of reducing LDL-cholesterol concentrations, and raising concentrations of HDL-cholesterol, as well as being of high pharmacological safety; and (2) providing an antihyperlipidemic composition comprising, as an active ingredient, the compound possessing the aforementioned superior characteristics.

DESCRIPTION OF THE PREFERRED EMBODIMENTS

Representative examples of the compounds of the present invention are shown in Table 1.

TABLE 1

| Compound No. | $R^1$ | $R^2$ | Molecular formula | Melting point (°C.) |
|---|---|---|---|---|
| 1 | —CH$_2$CH$_3$ | H | C$_{19}$H$_{29}$NO$_2$ | 210–214 |
| 2 | —CH$_2$CH$_2$CH$_3$ | H | C$_{20}$H$_{31}$NO$_2$ | 189–192 |
| 3 | —CH$_2$CH$_2$CH$_2$CH$_3$ | H | C$_{21}$H$_{33}$NO$_2$ | 156–157 |
| 4 | —CH$_2$CH$_2$CH$_2$CH$_3$ | —CH$_2$CH$_2$CH$_2$CH$_3$ | C$_{25}$H$_{41}$NO$_2$ | 179–180 |
| 5 | —CH(CH$_2$CH$_2$CH$_3$)$_2$ | H | C$_{24}$H$_{39}$NO$_2$ | 178–181 |
| 6 | —CH$_2$CO$_2$C$_2$H$_5$ | H | C$_{21}$H$_{31}$NO$_4$ | 168–169 |
| 7 | —CH$_2$CO$_2$H | H | C$_{19}$H$_{29}$NO$_4$ | 223–225 |
| 8 | —CH$_2$CONH(n-Bu) | H | C$_{23}$H$_{36}$N$_2$O$_3$ | 84–87 |
| 9 | —CH$_2$CONHCH$_2$C$_6$H$_5$ | H | C$_{26}$H$_{34}$N$_2$O$_3$ | 166–168 |
| 10 | —CH$_2$CON(piperazinyl)N(n-Bu) | H | C$_{27}$H$_{43}$N$_3$O$_3$ | 189–190 |
| 11 | —CH$_2$CON(piperazinyl)NCH$_2$C$_6$H$_5$ | H | C$_{30}$H$_{41}$N$_3$O$_3$ | 115–118 |
| 12 | —CH$_2$CON(piperazinyl)N-(2-pyridyl) | H | C$_{28}$H$_{38}$N$_4$O$_3$ | 188–194 |

TABLE 1-continued

| | | | | |
|---|---|---|---|---|
| 13 | —CH$_2$CH$_2$CH$_2$CO$_2$H | n-Bu | C$_{25}$H$_{39}$NO$_4$ | Oily liquid |
| 14 | —CH$_2$CO$_2$C$_2$H$_5$ | n-Bu | C$_{25}$H$_{39}$NO$_4$ | 100–105 |
| 15 | —CH$_2$CH(CH$_2$OH)CO$_2$CH$_3$ | n-Bu | C$_{26}$H$_{41}$NO$_5$ | 52–54 |
| 16 | —CH$_2$CON(piperazinyl)NCH$_2$C$_6$H$_5$ | n-Bu | C$_{34}$H$_{49}$N$_3$O$_3$ | 78–80 |
| 17 | —CH$_2$CON(piperazinyl)N-(2-pyridyl) | n-Bu | C$_{32}$H$_{46}$N$_4$O$_3$ | 60–65 |
| 18 | —CH$_2$CONHNH-C$_6$H$_5$ | n-Bu | C$_{29}$H$_{41}$N$_3$O$_3$ | 161–165 |
| 19 | —CH(CH$_2$CH(CH$_3$)$_2$)CO$_2$C$_2$H$_5$ | H | C$_{25}$H$_{39}$NO$_4$ | 148–151 |
| 20 | —CH(CH$_2$CH$_2$CO$_2$H)COOH | H | C$_{22}$H$_{31}$NO$_6$ | 102–103 |
| 21 | —CH(CO$_2$CH$_3$)-C$_6$H$_4$-OH | H | C$_{26}$H$_{33}$NO$_5$ | 110–111 |
| 22 | —CH(CO$_2$H)-C$_6$H$_4$-OH | H | C$_{25}$H$_{31}$NO$_5$ | 240–241 |
| 23 | —CH(CO$_2$C$_2$H$_5$)-C$_6$H$_5$ | H | C$_{27}$H$_{35}$NO$_4$ | 74–76 |
| 24 | —CH(CH$_2$OH)CON(piperazinyl)N—CH$_2$C$_6$H$_5$ | H | C$_{31}$H$_{43}$N$_3$O$_4$ | 102–105 |
| 25 | —CH$_2$CH$_2$OCH$_3$ | H | C$_{20}$H$_{31}$NO$_3$ | 148–150 |
| 26 | —CH$_2$CH$_2$OH | n-Bu | C$_{23}$H$_{37}$NO$_3$ | 122–123 |
| 27 | —CH$_2$CH$_2$OCONH(n-Bu) | n-Bu | C$_{28}$H$_{46}$N$_2$O$_4$ | 138–141 |
| 28 | —CH$_2$CH$_2$OCO-(4-pyridyl) | n-Bu | C$_{29}$H$_{40}$N$_2$O$_4$ | Oily liquid |
| 29 | —CH$_2$CH$_2$OCO-C$_6$H$_4$-Cl | n-Bu | C$_{30}$H$_{40}$NO$_4$Cl | 102–104 |
| 30 | —CH$_2$CH$_2$OCH$_3$ | —CH$_2$C$_6$H$_5$ | C$_{27}$H$_{37}$NO$_3$ | 104–105 |
| 31 | —CH$_2$CH$_2$SH | H | C$_{19}$H$_{29}$NO$_2$S | 160–161 |
| 32 | —CH$_2$CH$_2$S-(1-methylimidazol-2-yl) | H | C$_{23}$H$_{33}$N$_3$O$_2$S | 130–133 |

TABLE 1-continued

| | | | | |
|---|---|---|---|---|
| 33 | 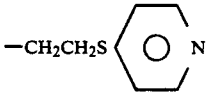 —CH$_2$CH$_2$S-(pyridinyl) | H | C$_{24}$H$_{32}$N$_2$O$_2$S | 88-93 |
| 34 | —CH$_2$CH$_2$SC$_6$H$_5$ | H | C$_{25}$H$_{33}$NO$_2$S | 99-100 |
| 35 |  —CH$_2$CH$_2$S-(pyrimidinyl) | H | C$_{23}$H$_{31}$N$_3$O$_2$S | 160-161 |
| 36 | 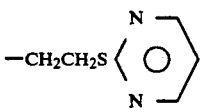 —CH$_2$CH$_2$S-(benzimidazolyl) | H | C$_{26}$H$_{33}$N$_3$O$_2$S | 110-114 |
| 37 | —CH$_2$CH$_2$SCH$_2$CO$_2$C$_2$H$_5$ | n-Bu | C$_{27}$H$_{43}$NO$_4$S | 91-92 |
| 38 | 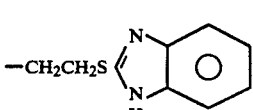 —CH$_2$CH$_2$SCH$_2$CONH-(thiazolyl) | n-Bu | C$_{28}$H$_{41}$N$_3$O$_3$S | 64-65 |
| 39 |  —CH$_2$CH$_2$S-(imidazolyl) | n-Bu | C$_{27}$H$_{39}$N$_3$O$_2$S | 107-110 |
| 40 | 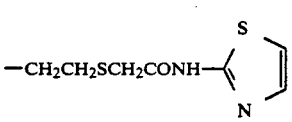 —(CH$_2$)$_2$NH-C$_6$H$_4$-CO$_2$C$_2$H$_5$ | H | C$_{28}$H$_{38}$N$_2$O$_4$ | 91-94 |
| 41 | —CH$_2$CH$_2$NH-C$_6$H$_5$ | H | C$_{25}$H$_{34}$N$_2$O$_2$ | 112-113 |
| 42 | 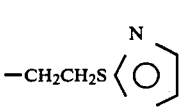 —CH$_2$CH$_2$NH-C$_6$H$_4$-CO$_2$H | n-Bu | C$_{30}$H$_{42}$N$_2$O$_2$ | 109-112 |
| 43 | 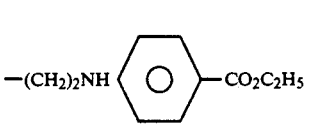 —CH$_2$CH$_2$NH-C$_6$H$_4$-CO$_2$Et | n-Bu | C$_{32}$H$_{46}$N$_2$O$_4$ | 113-116 |
| 44 |  —CH$_2$CH$_2$NHCO-(pyridinyl) | —CH$_2$C$_6$H$_5$ | C$_{32}$H$_{39}$N$_3$O$_3$ | 114-117 |
| 45 | —CHC$_6$H$_5$<br>   \|<br>  CH$_2$OH | H | C$_{25}$H$_{33}$NO$_3$ | 181-182 |
| 46 | —CHC$_6$H$_5$<br>   \|<br>  CH$_2$OH | n-Bu | C$_{29}$H$_{41}$NO$_3$ | 56-59 |
| 47 | —CH$_2$CHOH<br>      \|<br>    CH$_2$OH | n-Bu | C$_{24}$H$_{39}$NO$_4$ | 54-58 |
| 48 | —CH—C$_6$H$_5$<br>   \|<br>  CH$_3$ | H | C$_{25}$H$_{33}$NO$_2$ | 165-167 |
| 49 | —CH—C$_6$H$_5$<br>   \|<br>  CN | H | C$_{25}$H$_{30}$N$_2$O$_2$ | 90-94 |

TABLE 1-continued

| | | | | |
|---|---|---|---|---|
| 50 | 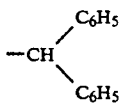 —CH(C₆H₅)₂ | H | $C_{30}H_{35}NO_2$ | 225–226 |
| 51 | 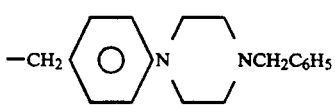 —CH₂–⟨C₆H₄⟩–N(piperazine)NCH₂C₆H₅ | n-Bu | $C_{39}H_{53}N_3O_2$ | 57–60 |
| 52 | 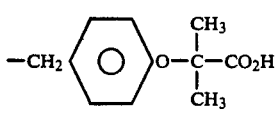 —CH₂–⟨C₆H₄⟩–O–C(CH₃)₂–CO₂H | n-Bu | $C_{32}H_{45}NO_5$ | 159–161 |
| 53 | 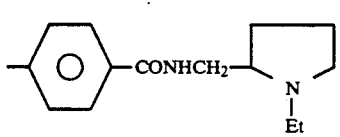 —⟨C₆H₄⟩–CONHCH₂–(N-Et pyrrolidine) | n-Bu | $C_{35}H_{51}N_3O_3$ | 145–146 |
| 54 | 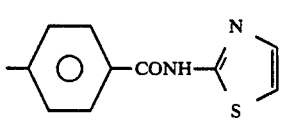 —⟨C₆H₄⟩–CONH–(thiazole) | n-Bu | $C_{31}H_{39}N_3O_3S$ | 207–211 |
| 55 | 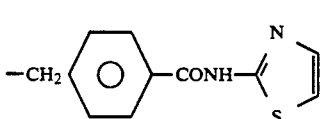 —CH₂–⟨C₆H₄⟩–CONH–(thiazole) | n-Bu | $C_{32}H_{41}N_3O_3S$ | 172–173 |
| 56 | —CH₂CH₂CN | H | $C_{20}H_{28}N_2O_2$ | 182–185 |
| 57 | —CH₂C₆H₅ | H | $C_{24}H_{31}NO_2$ | 164–165 |
| 58 | —CH₂CH₂C₆H₅ | H | $C_{25}H_{33}NO_2$ | 157–160 |
| 59 |  —CH₂–⟨C₆H₄⟩–NO₂ | H | $C_{24}H_{30}N_2O_4$ | 158–159 |
| 60 | 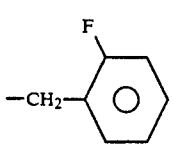 —CH₂–⟨C₆H₄⟩–F | H | $C_{24}H_{30}NO_2F$ | 147–148 |
| 61 | 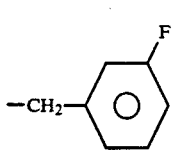 —CH₂–⟨C₆H₄⟩–F | H | $C_{24}H_{30}NO_2F$ | 130–135 |
| 62 | 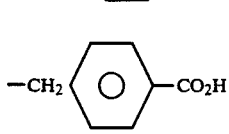 —CH₂–⟨C₆H₄⟩–CO₂H | H | $C_{25}H_{31}NO_4$ | 207–210 |
| 63 | 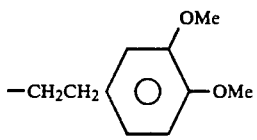 —CH₂CH₂–⟨C₆H₃⟩(OMe)(OMe) | H | $C_{27}H_{37}NO_4$ | 80–84 |
| 64 | 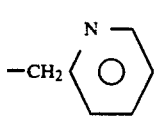 —CH₂–(pyridyl) | H | $C_{23}H_{30}N_2O_2$ | 190–191 |

TABLE 1-continued

| # | R | R' | Formula | mp (°C) |
|---|---|---|---|---|
| 65 | -CH₂CH₂-(3-pyridyl) | H | $C_{24}H_{32}N_2O_2$ | 139-140 |
| 66 | -CH₂CH₂CH₂-N(imidazolyl) | H | $C_{23}H_{33}N_3O_2$ | 178-181 |
| 67 | -CH₂-(2-thienyl) | H | $C_{22}H_{29}NO_2S$ | 170-171 |
| 68 | -CH₂-(3,5-di-tert-butyl-4-hydroxyphenyl) | H | $C_{32}H_{47}NO_3$ | 217-220 |
| 69 | -CH₂CH(OCH₃)₂ | H | $C_{21}H_{33}NO_4$ | 162-163 |
| 70 | -CH₂CN | n-Bu | $C_{23}H_{34}N_2O_2$ | 144-145 |
| 71 | -CH₂CH₂N(CH₃)₂ | n-Bu | $C_{25}H_{42}N_2O_2$ | 173-174 |
| 72 | -CH₂C₆H₅ | n-Bu | $C_{28}H_{39}NO_2$ | 128-130 |
| 73 | (3-pyridyl)- | n-Bu | $C_{26}H_{36}N_2O_2$ | 166-169 |
| 74 | -CH₂-(3-pyridyl) | n-Bu | $C_{27}H_{38}N_2O_2$ | 98-103 |
| 75 | -CH₂-(3-indolyl) | n-Bu | $C_{30}H_{40}N_2O_2$ | 77-79 |
| 76 | -CH₂-(3-methyl-2-thienyl) | n-Bu | $C_{21}H_{39}NO_2S$ | 94-96 |
| 77 | -CH₂-(3-pyridyl) | -CH₂C₆H₅ | $C_{30}H_{36}N_2O_2$ | 155-158 |
| 78 | -CH₂-(3-indolyl) | -CH₂C₆H₅ | $C_{33}H_{38}N_2O_2$ | 145-146 |
| 79 | -CH₂CH₂N(piperazinyl)-(2-pyridyl) | n-Bu | $C_{32}H_{48}N_4O_2$ | 141-142 |
| 80 | -C(CH₃)₂-CO₂CH₃ | H | $C_{22}H_{33}NO_4$ | 196-197 |

TABLE 1-continued

| # | Structure | R | Formula | mp |
|---|---|---|---|---|
| 81 | 3-methyl-γ-butyrolactone | H | $C_{21}H_{29}NO_4$ | 138–140 |
| 82 | decahydronaphthalen-1-yl | H | $C_{27}H_{35}NO_2$ | 186–187 |
| 83 | octahydroindan-2-yl | H | $C_{26}H_{33}NO_2$ | 120–121 |
| 84 | $-C(CH_3)_2-CO_2C_2H_5$ | n-Bu | $C_{27}H_{43}NO_4$ | 114–115 |
| 85 | $-COCH_3$ | $-CH_2C_6H_5$ | $C_{26}H_{33}NO_3$ | 103–105 |

$$-N\diagdown^{R^1}_{R^2}$$

| # | Structure | Formula | mp |
|---|---|---|---|
| 86 | -N(piperidinyl) | $C_{22}H_{33}NO_2$ | 163–166 |
| 87 | -N(morpholinyl) | $C_{21}H_{31}HO_3$ | 141–143 |
| 88 | -N(4-n-butylpiperazinyl) | $C_{25}H_{40}N_2O_2$ | 189–190 |
| 89 | -N(2-ethoxycarbonylpiperidinyl) | $C_{25}H_{37}NO_4$ | 157–158 |
| 90 | -N(3-ethoxycarbonylpiperidinyl) | $C_{25}H_{37}NO_4$ | 164–165 |
| 91 | -N(2-carboxypiperidinyl) | $C_{23}H_{33}NO_4$ | 201–205 |
| 92 | -N(4-benzylpiperazinyl) | $C_{28}H_{38}N_2O_2$ | 158–159 |

TABLE 1-continued
| 93 | 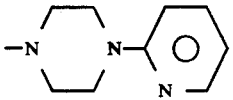 | | | | $C_{26}H_{35}N_3O_2$ | 147-150 |
| | Elementary analysis (%) | | | | | |
| --- | --- | --- | --- | --- | --- | --- |
| | C | | H | | N | |
| Compound No. | Experimental value | Theoretical value | Experimental value | Theoretical value | Experimental value | Theoretical value |
| 1 | 75.37 | 75.20 | 9.58 | 9.63 | 4.85 | 4.62 |
| 2 | 75.39 | 75.67 | 9.99 | 9.84 | 4.26 | 4.41 |
| 3 | 75.91 | 76.09 | 10.05 | 10.03 | 4.51 | 4.23 |
| 4 | 77.63 | 77.47 | 10.77 | 10.67 | 3.42 | 3.61 |
| 5 | 77.37 | 77.16 | 10.34 | 10.52 | 3.41 | 3.75 |
| 6 | 69.58 | 69.77 | 8.60 | 8.65 | 3.71 | 3.88 |
| 7 | 68.72 | 68.44 | 8.25 | 8.16 | 3.97 | 4.20 |
| 8 | 71.37 | 71.10 | 9.26 | 9.34 | 7.54 | 7.21 |
| 9 | 74.15 | 73.90 | 8.03 | 8.11 | 6.91 | 6.63 |
| 10 | 70.97 | 70.86 | 9.41 | 9.47 | 9.39 | 9.18 |
| 11 | 73.53 | 73.28 | 8.29 | 8.41 | 8.23 | 8.55 |
| 12 | 69.85 | 70.26 | 7.71 | 8.00 | 12.14 | 11.71 |
| 13 | 71.51 | 71.89 | 9.27 | 9.41 | 3.63 | 3.36 |
| 14 | 71.67 | 71.89 | 9.70 | 9.41 | 3.78 | 3.36 |
| 15 | 69.48 | 69.76 | 9.37 | 9.23 | 3.44 | 3.13 |
| 16 | 74.24 | 74.55 | 9.16 | 9.02 | 7.32 | 7.67 |
| 17 | 72.26 | 71.87 | 8.60 | 8.67 | 10.84 | 10.48 |
| 18 | 72.99 | 72.61 | 8.50 | 8.62 | 9.18 | 8.76 |
| 19 | 71.57 | 71.89 | 9.56 | 9.41 | 3.03 | 3.36 |
| 20 | 65.27 | 65.16 | 7.74 | 7.71 | 3.27 | 3.45 |
| 21 | 70.88 | 71.04 | 7.73 | 7.57 | 3.27 | 3.19 |
| 22 | 70.39 | 70.56 | 7.39 | 7.34 | 3.41 | 3.29 |
| 23 | 74.36 | 74.11 | 7.81 | 8.06 | 3.53 | 3.20 |
| 24 | 71.71 | 71.37 | 8.39 | 8.31 | 8.42 | 8.06 |
| 25 | 71.74 | 72.03 | 9.18 | 9.37 | 4.53 | 4.20 |
| 26 | 73.43 | 73.56 | 9.89 | 9.93 | 3.91 | 3.73 |
| 27 | 70.52 | 70.85 | 9.48 | 9.77 | 5.59 | 5.90 |
| 28 | 72.83 | 72.47 | 8.27 | 8.39 | 5.48 | 5.83 |
| 29 | 70.39 | 70.09 | 7.76 | 7.84 | 2.34 | 2.72 |
| 30 | 76.71 | 76.56 | 8.69 | 8.81 | 3.50 | 3.31 |
| 31 | 68.29 | 68.03 | 8.86 | 8.71 | 3.81 | 4.18 |
| 32 | 66.72 | 66.48 | 8.27 | 8.01 | 10.45 | 10.11 |
| 33 | 69.44 | 69.88 | 7.97 | 7.82 | 6.46 | 6.99 |
| 34 | 73.04 | 72.96 | 8.12 | 8.08 | 3.30 | 3.40 |
| 35 | 66.69 | 66.80 | 7.64 | 7.56 | 10.01 | 10.16 |
| 36 | 68.77 | 69.15 | 7.53 | 7.37 | 9.67 | 9.31 |
| 37 | 67.58 | 67.89 | 9.14 | 9.07 | 2.77 | 2.93 |
| 38 | 63.11 | 63.25 | 7.68 | 7.77 | 7.58 | 7.90 |
| 39 | 68.77 | 69.05 | 8.18 | 8.37 | 9.29 | 8.95 |
| 40 | 72.46 | 72.07 | 8.03 | 8.21 | 5.61 | 6.00 |
| 41 | 76.25 | 76.10 | 8.59 | 8.69 | 7.31 | 7.10 |
| 42 | 72.45 | 72.84 | 8.78 | 8.56 | 5.28 | 5.66 |
| 43 | 73.81 | 73.53 | 8.69 | 8.87 | 5.00 | 5.36 |
| 44 | 74.51 | 74.82 | 7.83 | 7.65 | 7.77 | 8.18 |
| 45 | 75.78 | 75.91 | 8.43 | 8.41 | 3.29 | 3.54 |
| 46 | 77.36 | 77.12 | 9.41 | 9.15 | 2.80 | 3.10 |
| 47 | 71.39 | 71.07 | 9.33 | 9.69 | 3.18 | 3.45 |
| 48 | 79.32 | 79.11 | 8.70 | 8.76 | 3.98 | 3.69 |
| 49 | 76.51 | 76.89 | 7.59 | 7.74 | 7.55 | 7.17 |
| 50 | 81.64 | 81.59 | 8.05 | 7.99 | 3.31 | 3.17 |
| 51 | 78.32 | 78.61 | 8.84 | 8.97 | 7.41 | 7.05 |
| 52 | 73.22 | 73.39 | 8.51 | 8.66 | 2.83 | 2.67 |
| 53 | 74.68 | 74.82 | 9.27 | 9.15 | 7.61 | 7.48 |
| 54 | 69.42 | 69.79 | 7.10 | 7.37 | 8.25 | 7.87 |
| 55 | 70.24 | 70.17 | 7.49 | 7.55 | 7.31 | 7.67 |
| 56 | 73.41 | 73.13 | 8.37 | 8.59 | 8.28 | 8.53 |
| 57 | 78.75 | 78.86 | 8.61 | 8.55 | 3.68 | 3.84 |
| 58 | 79.41 | 79.11 | 9.01 | 8.76 | 3.31 | 3.69 |
| 59 | 70.03 | 70.22 | 7.31 | 7.37 | 6.51 | 6.82 |
| 60 | 75.28 | 75.17 | 7.93 | 7.89 | 3.51 | 3.65 |
| 61 | 75.55 | 75.17 | 7.83 | 7.89 | 3.24 | 3.65 |
| 62 | 73.63 | 73.32 | 7.92 | 7.83 | 3.08 | 3.42 |
| 63 | 73.99 | 73.77 | 8.21 | 8.48 | 3.54 | 3.19 |
| 64 | 75.21 | 75.37 | 8.23 | 8.25 | 7.78 | 7.64 |
| 65 | 75.81 | 75.75 | 8.39 | 8.48 | 7.51 | 7.35 |
| 66 | 71.89 | 72.02 | 8.58 | 8.67 | 10.73 | 10.96 |
| 67 | 70.82 | 71.13 | 7.77 | 7.87 | 3.53 | 3.77 |
| 68 | 77.53 | 77.84 | 9.82 | 9.60 | 2.47 | 2.84 |
| 69 | 69.48 | 69.39 | 9.20 | 9.15 | 3.67 | 3.85 |
| 70 | 74.70 | 74.55 | 9.36 | 9.25 | 7.28 | 7.56 |
| 71 | 74.46 | 74.58 | 10.55 | 10.52 | 6.81 | 6.96 |
| 72 | 79.63 | 79.76 | 9.41 | 9.32 | 3.10 | 3.32 |

TABLE 1-continued

| | | | | | | |
|---|---|---|---|---|---|---|
| 73 | 76.74 | 76.43 | 9.17 | 8.88 | 7.06 | 6.86 |
| 74 | 77.08 | 76.63 | 9.28 | 9.06 | 6.19 | 6.63 |
| 75 | 78.49 | 78.22 | 8.63 | 8.75 | 6.40 | 6.08 |
| 76 | 73.21 | 73.43 | 8.78 | 8.90 | 3.42 | 3.17 |
| 77 | 79.27 | 78.91 | 8.11 | 7.95 | 5.82 | 6.14 |
| 78 | 80.24 | 80.12 | 7.65 | 7.74 | 5.49 | 5.66 |
| 79 | 73.72 | 73.80 | 9.34 | 9.29 | 10.92 | 10.76 |
| 80 | 70.51 | 70.37 | 8.77 | 8.86 | 3.84 | 3.73 |
| 81 | 70.01 | 70.17 | 8.30 | 8.13 | 3.66 | 3.90 |
| 82 | 80.02 | 79.96 | 8.71 | 8.70 | 3.23 | 3.45 |
| 83 | 79.58 | 79.75 | 8.60 | 8.50 | 3.43 | 3.58 |
| 84 | 72.43 | 72.77 | 9.68 | 9.73 | 3.36 | 3.14 |
| 85 | 76.91 | 76.62 | 8.03 | 8.16 | 3.29 | 3.44 |
| 86 | 76.58 | 76.92 | 9.44 | 9.68 | 4.39 | 4.08 |
| 87 | 73.27 | 73.00 | 8.91 | 9.05 | 4.27 | 4.05 |
| 88 | 75.12 | 74.95 | 10.21 | 10.07 | 7.25 | 6.99 |
| 89 | 72.31 | 72.25 | 8.96 | 8.98 | 3.48 | 3.37 |
| 90 | 72.17 | 72.25 | 9.02 | 8.98 | 3.45 | 3.37 |
| 91 | 71.57 | 71.29 | 8.37 | 8.58 | 3.30 | 3.61 |
| 92 | 77.25 | 77.38 | 8.88 | 8.81 | 6.17 | 6.45 |
| 93 | 74.32 | 74.07 | 8.48 | 8.37 | 9.61 | 9.97 |

The cinnamamide derivatives I of the present invention form salts with bases. Furthermore, the cinnamamide derivatives of the present invention can also form salts with acids in the following cases.

(i) When $R^1$ is of the formula $-(CH_2)_n1COR^3$, wherein $R^3$ is

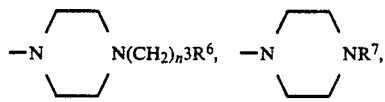

or $-NHNHC_6H_5$.

(ii) When $R^1$ is of the formula

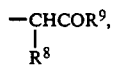

wherein $R^9$ is

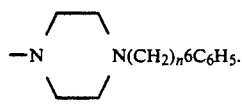

(iii) When $R^1$ is of the formula $-(CH_2)_n7COR^{12}$, wherein $R^{12}$ is of the formula $-COR^{14}$ ($R^{14}$ is pyridyl).

(iv) When $R^1$ is of the formula $-(CH_2)_n8SR^{15}$, wherein $R^{15}$ is

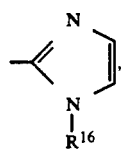

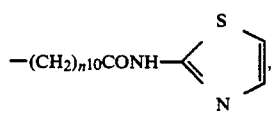

or $-(CH_2)_n11R^{18}$ ($R^{18}$ is pyridyl, pyrimidyl, or benzimidazolyl).

(v) When $R^1$ is of the formula $-(CH_2)_n12NHR^{19}$.

(vi) When $R^1$ is of the formula

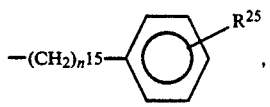

wherein $R^{25}$ is

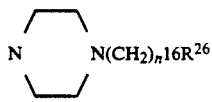

or $-CONH(CH_2)_n17R^{27}$ ($R^{27}$ is pyrrolidyl substituted by alkyl containing 1-3 carbon atoms, or thiazolyl).

(vii) When $R^1$ is of the formula $-(CH_2)_n18R^{28}$ or

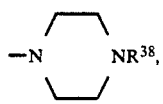

wherein $R^{28}$ is imidazolyl, pyridyl, or

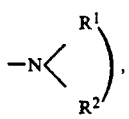

(vii) When $R^1$ and $R^2$ are linked together with the nitrogen atoms of the amide group, forming a ring of $$-N\diagdown\genfrac{}{}{0pt}{}{R^1}{R^2}\diagup$$

which is

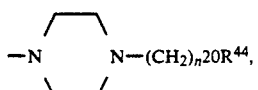

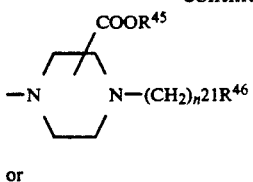

or

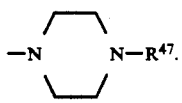

The salts of cinnamamide derivatives of the present invention include, for example, the following.
(1) Salts with various metals, such as alkaline metals, alkali earth metals, or aluminum.
(2) Ammonium salts.
(3) Salts with organic bases such as methylamine, ethylamine, diethylamine, triethylamine, pyrrolidine, piperidine, morpholine, hexamethyleneimine, aniline or pyridine.
(4) Salts with organic acids such as formic acid, acetic acid, trichloroacetic acid, maleic acid, tartaric acid, methanesulfonic acid, benzenesulfonic acid, or toluenesulfonic acid.
(5) Salts with inorganic acids such as hydrochloric acid, hydrobromic acid, sulfonic acid, or phosphoric acid.
(6) Salts with amino acids such as arginine, glutamic acid, or ornithine.

When salts of the above types are to be contained in antihyperlipidemic composition, pharmaceutically acceptable salts are selected.

The cinnamamide derivatives of formula I of the present invention, can be synthesized, for example, by either the first or second of the following methods.

In the first method, the cinnamamide derivative I is obtained by a reaction between a compound of formula II and a compound of formula III.

wherein $R^{48}$ is hydrogen, or alkyl containing 1–4 carbon atoms.

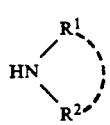 (III)

wherein $R^1$ and $R^2$ are the same as those of formula I.

The reaction between the compound II and the compound III is conducted without a catalyst, in the presence of a dehydrating condensing agent or a base. The aforementioned dehydrating condensing agents applicable for the present purpose include conventional dehydrating condensing agents such as dicyclohexylcarbodiimide, and 1-ethyl-3-(3-dimethylaminopropyl)carbodiimide. The applicable bases include, for example, metal alcoholates such as sodium methoxide, alkyl metal compounds such as butyllithium, or metal hydrides such as sodium hydride. Alternatively, the compound of formula II can be converted to an acyl halide by means of a halogenating reagent such as phosphorus pentachloride or thionyl chloride. Then this acyl halide is allowed to react with the compound of formula III, thereby obtaining the desired cinnamamide derivative I.

Cinnamamide derivatives I in which $R^1$ is —$(CH_2)_{n1}COR^3$ ($R^3$ is —$OR^4$) can be hydrolyzed by conventional methods using an acid or base catalyst, thereby obtaining a cinnamamide derivative having a carboxylic group, wherein $R^3$ is hydroxyl. Furthermore, the derivative having a carboxyl group so obtained can be treated with $NH_2R^5$, $NH_2(CH_2)_{n2}$—$C_6H_5$,

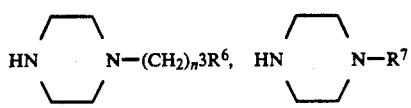

or $NH_2NH$—$C_6H_5$, thereby obtaining a compound wherein $R_3$ is —$NHR^5$, —$NH(CH_2)_{n2}$—$C_6H_5$,

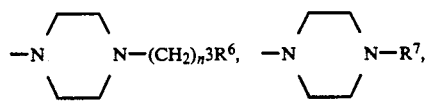

or —$NHNHC_6H_5$. In the above formulae, $R^5$, $n^2$, $R^6$ and $R^7$ are the same as those of formula I.

Furthermore, in the case where $R^1$ is

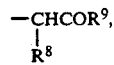

$R^8$ is —$(CH_2)_{n4}CO_2R^{10}$ and $R^{10}$ is alkyl with 1–3 carbon atoms, then the cinnamamide derivative can be hydrolyzed by conventional methods using an acid or base catalyst, thereby obtaining a cinnamamide derivative having a carboxyl group, wherein $R^{10}$ is hydrogen. In the case where $R^1$ is

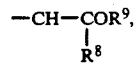

and $R^9$ is —$OR^{11}$, then the cinnamamide derivative can further be hydrolyzed by conventional methods using an acid or base catalyst, thereby obtaining a cinnamamide derivative having carboxyl group, wherein $R^9$ is hydroxyl. Furthermore, the derivative having a carboxyl group obtained in this manner can be treated with

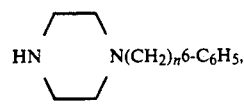

thereby obtaining a compound wherein $R^9$ is

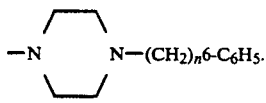

Furthermore, in the case where $R^1$ is $-(CH_2)_n8SR^{15}$ and $R^{15}$ is $-(CH_2)_n9COOR^{17}$, the cinnamamide derivative can be hydrolyzed by conventional methods using an acid or base catalyst, and the resulting cinnamamide derivative having a carboxyl group so obtained can be treated with 2-aminothiazole, thereby obtaining a derivative wherein $R^{15}$ is

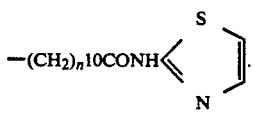

In the case where $R^1$ and $R^2$ are linked together with the amide nitrogen to form a ring of

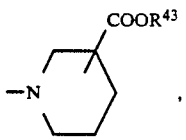

wherein $R^{43}$ is alkyl with 1-3 carbon atoms, then the cinnamamide derivative can be hydrolyzed by conventional methods using an acid or base catalyst, thereby obtaining a cinnamamide derivative having a carboxyl group, wherein $R^{43}$ is hydrogen.

In the case where $R^1$ and $R^2$ are linked together with the amide nitrogen to form a ring of

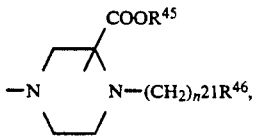

wherein $R^{45}$ is alkyl with 1-3 carbon atoms, then the cinnamamide derivative can be hydrolyzed by conventional methods using an acid or base catalyst, thereby obtaining a cinnamamide derivative having a carboxyl group, wherein $R^{45}$ is hydrogen.

In the second method, the aforementioned cinnamamide derivative I is synthesized by a Wittig reaction in which an aldehyde is allowed to react with a ylide. In the reaction, 3,5-di-tert-butyl-4-hydroxybenzaldehyde can be used as the aldehyde, and, for example, a compound of the following formula IV can be used as the ylide.

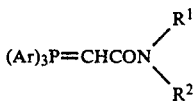 (IV)

wherein $R^1$ and $R^2$ are the same as in formula I.

In addition to the compound of formula IV, ylides derived from trialkylphosphines or triarylarsines can be used for the present purpose.

Among the cinnamamide derivatives I, those such that $R^1$ is

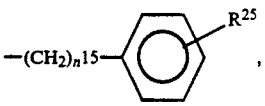

and $R^{25}$ is $-CONH(CH_2)_n17R^{27}$, can be synthesized by the following method. First, a compound in which $R^{25}$ is $-CO_2R^{49}$ (wherein $R^{49}$ is alkyl with 1-3 carbon atoms) is obtained by either the first or second of the aforementioned methods, then this product is converted into the corresponding carboxylic acid by hydrolysis with an acid or base catalyst in the same manner as indicated above. The carboxylic acid so obtained is allowed to react with a pyrrolidylalkylamine or a thiazolylalkylamine, thereby obtaining the desired cinnamamide derivative.

The cinnamamide derivatives of the present invention and the pharmaceutically acceptable salts of these compounds are effective as antihyperlipidemic agents, and, moreover, are of extremely low toxicity with respect to the living body. This will be apparent from the results of the experiments to be described below. Antihyperlipidemic composition containing these cinnamamide derivatives or their salts can be administered either orally or parenterally. The aforementioned composition generally contains a suitable carrier (i.e., excipient). Such composition includes tablets, capsules, fine granules, syrups, suppositories, ointments, and injections. The aforementioned carrier is an organic or inorganic solid or liquid whichever is appropriate for the preparation of the desired form of the composition suitable for oral or parenteral administration. Ordinarily, an inert pharmaceutical excipient is used for this purpose. These excipients include crystalline cellulose, gelatin, lactose, starch, magnesium stearate, talc, vegetable or animal fats or oils, gums, and polyalkyleneglycols. The antihyperlipidemic composition of the present invention contains the aforementioned cinnamamide derivatives and/or their salts in a proportion ranging from 0.2% by weight to 100% by weight. The antihyperlipidemic composition may also contain other drugs (including antihyperlipidemic agents), provided that these other drugs do not diminish the efficacy of the aforementioned cinnamamide derivatives and/or their salts. In such cases, the aforementioned cinnamamide derivatives or their salts need not necessarily be the principal ingredients of the said preparation.

The antihyperlipidemic compositions of the present invention are generally to be administered at dosages such that the desired effects are attained without the occurrence of any side effects. The specific doses to be administered will vary according to factors such as the severity of the illness and the age of the patient, and should be determined in accordance with the judgment of the attending physician in every case. However, the aforementioned cinnamamide derivatives and/or their salts should be administered in doses within the range of 1 mg−5 g, and preferably 3 mg−1 g for an adult per day. Thus, the administered amount of the actual drug preparation, including the excipient, should ordinarily be in the range of 10 mg−10 g, and preferably 20 mg−5 g.

(EXAMPLES)

The present invention will be explained with reference to the following examples.

EXAMPLE 1

Synthesis of Compound 3 (hereinafter, compounds are numbered as in Table 1)

A solution of 2.95 g of 3,5-di-t-butyl-4-hydroxycinnamyl chloride dissolved in 10 ml of THF was added to a mixed solution of 2.19 g of n-butylamine and 10 ml of THF under ice cooling, and the mixture was agitated for 3 hours. Then, 100 ml of ether was added and the mixture was washed twice with water. The organic layer was dehydrated with sodium sulfate, evaporated to dryness, after which recrystallization from a mixed solvent of benzene and n-hexane yielded 1.5 g of the desired Compound 3.

EXAMPLE 2

Synthesis of Compound 6

First, 2.79 g of glycine ethyl ester hydrochloride, 3.9 ml of triethylamine and 4.20 g of 1- ethyl-3-(3-dimethylaminopropyl)carbodiimide hydrochloride were added to 140 ml of a dichloromethane solution containing 5.52 g of 3,5-di-t-butyl-4-hydroxycinnamic acid, and the mixture was allowed to react for 5 hours at room temperature. Then, water was added to the reaction mixture and the mixture was extracted with chloroform several times. The organic layers were combined, washed with water and concentrated under reduced pressure. Then, a mixed solvent of methylene chloride and n-hexane was added to the residue, and 5.9 g of the desired Compound 6 was obtained by crystallization (yield 75%).

EXAMPLE 3

Synthesis of Compound 7

First, 722 mg of the Compound 6 obtained in Example 2 was dissolved in 20 ml of methanol, 4.5 ml of a 1N aqueous solution of sodium hydroxide was added to the mixture, and the mixture was allowed to react at room temperature for 3 hours. The reaction mixture was then poured onto ice water and acidified with dilute hydrochloric acid. After chloroform extraction, the chloroform layers were combined, dehydrated with sodium sulfate, and then concentrated under reduced pressure. Ethyl acetate was added to the concentrate, and 460 mg of the desired Compound 7 was obtained by crystallization (yield 69%).

EXAMPLE 4

Synthesis of Compound 14

First, 14.0 g of glycine ethyl ester hydrochloride, 13.7 g of n-butyl bromide and 14 ml of triethylamine were refluxed overnight in ethanol. Then, an aqueous solution of sodium bicarbonate was added to this mixture, which was then extracted with chloroform. The organic layer was dehydrated and concentrated. The concentrate so obtained, together with 16.6 g of 3,5-di-t-butyl-4-hydroxycinnamic acid, was added to 300 ml of methylene chloride. To this mixture, 8.4 ml of triethylamine and 12.6 g of 1-ethyl- 3-(3-dimethylaminopropyl)carbodiimide hydrochloride were added, and the mixture so obtained was allowed to react for 5 hours at room temperature.

After washing with 300 ml of dilute hydrochloric acid, the reaction mixture was also washed with water and then concentrated under reduced pressure. The residue was subjected to column chromatography using silica gel as a carrier, eluted with chloroform, the fraction containing the desired compound was collected, and the solvent was distilled off, thereby obtaining 8 g of the desired Compound 14 (yield 32%).

EXAMPLE 5

Synthesis of Compound 15

First, 3.3 g of 3,5-di-t-butyl-4-hydroxycinnamic acid and 2.1 g of N-butylserine methyl ester were dissolved in 50 ml of dichloromethane, then, 2.9 g of 1-ethyl-3-(3-dimethylaminopropyl)carbodiimide hydrochloride was added to the mixture, and the mixture so obtained was allowed to react for 2 hours at room temperature. This reaction mixture was washed twice with 50 ml of water and concentrated under reduced pressure. The concentrate was subjected to column chromatography using silica gel as a carrier, eluted with chloroform, the fraction containing the desired compound was collected, and the solvent was distilled off, thereby obtaining 3.2 g of the desired Compound 15 (yield 62%).

EXAMPLE 6

Synthesis of Compound 16

First, 1.5 g of N-n-butyl—N-carboxymethyl-3,5-di-t-butyl-4-hydroxycinnamamide prepared by hydrolyzing Compound 14 with sodium hydroxide, together with 0.69 g of N-benzylpiperazine, was added to 40 ml of dichloromethane. Then, 0.82 g of 1-ethyl-3-(3-dimethylaminopropyl)carbodiimide hydrochloride was added to the mixture so obtained and the mixture was allowed to react for 5 hours at room temperature. After completion of the reaction, the reaction mixture was washed twice with water and concentrated under reduced pressure. The concentrate so obtained was subjected to column chromathography using silica gel as a carrier, eluted with chloroform containing 2% methanol, the fraction containing the desired compound was collected, and the solvent was distilled off, thereby obtaining 0.97 g of the desired Compound 16 (yield 46%).

EXAMPLE 7

Synthesis of Compound 19

First, 3.91 g of L-leucine ethyl ester hydrochloride, 3.1 ml of triethylamine and 4.20 g of 1-ethyl-3-(3-dimethylaminopropyl)carbodiimide hydrochloride were added to 140 ml of a dichloromethane solution containing 5.52 g of 3,5-di-t-butyl-4-hydroxycinnamic acid, and the mixture was allowed to react for 5 hours at room temperature. Then, water was added to the reaction mixture and the mixture was extracted with chloroform several times. The organic layers were combined, first washed with dilute hydrochloric acid, and then with water and evaporated to dryness under reduced pressure. The residue was subjected to column chromathography using silica gel as a carrier, eluted with chloroform, the fraction containing the desired compound was collected, and the solvent was distilled off, thereby obtaining 5.0 g of the desired Compound 19 (yield 68%).

EXAMPLE 8

Synthesis of Compound 21

First, 6.0 g of 3,5 TM di-t-butyl-4-hydroxycinnamic acid and 4,8 g of 4-hydroxyphenylglycine methyl ester hydrochloride were suspended in 100 ml of dichloromethane, and 4 5 g of 1-ethyl-3-(3-dimethylaminopropyl)carbodiimide hydrochloride and 6.0 ml of triethylamine were added to the mixture sc obtained and the mixture was allowed to react for 2 hours at room temperature. After completion of the reaction, the reaction mixture was washed with water and concentrated to dryness. The residue was subjected to column chromathography using silica gel as a carrier, eluted with chloroform, the fraction containing the desired compound was collected, and the solvent was distilled off, thereby obtaining 7.6 g of the desired Compound 21 (yield 83%).

EXAMPLE 9

First, 2.0 g of the Compound 21 obtained in Example 8 was dissolved in 10 ml of ethanol, and 30 ml of 15% aqueous solution of sodium hydroxide was added. This reaction mixture was then heated at 60° C. and allowed to react for 2 hours. After cooling, the mixture was adjusted to pH 1 by the addition of 2N hydrochloric acid, and then extracted three times with 50 ml of chloroform. The organic layers were combined and dehydrated with magnesium sulfate, after which the solvent was distilled off under reduced pressure. Then, benzene was added to the residue and 1.5 g of the desired Compound 22 was obtained by crystallization (yield 79%).

EXAMPLE 10

Synthesis of Compound 24

First, 20 g of 3,5-di-t-butyl-4-hydroxycinnamic acid, 11.2 g of serine methyl ester hydrochloride, 13.6 g of 1-ethyl-3-(3-dimethylaminopropyl)carbodiimide hydrochloride, and 10 ml of triethylamine were added to 300 ml of dichloromethane, and then the mixture was allowed to react for 2 hours at room temperature. After completion of the reaction, this mixture was washed by addition of water, and the dichloromethane was distilled off under reduced pressure. The residue so obtained was separated and purified by column chromatography on silica gel using chloroform as an eluent, thereby obtaining 9.3 g of N-(3,5-di-t-butyl-4-hydroxycinnamyl)serine methyl ester.

The 9.3 g of N-(3,5-di-t-butyl-4-hydroxycinnamyl)serine methyl ester obtained in the aforementioned process and 24.6 ml of 1N sodium hydroxide were added to 90 ml of ethanol, and after mixing the mixture was allowed to react for 8 hours at room temperature. After completion of the reaction, this mixture was acidified with 2N hydrochloric acid, and then, chloroform was added. After mixing, the chloroform layer was separated and washed with water, and then the chloroform was distilled off under reduced pressure. The residue so obtained was separated and purified by column chromatography on silica gel using a chloroform-methanol 9:1 mixture as an eluent, thereby obtaining 8.5 g of N-(3,5-di-t-butyl-4-hydroxycinnamyl)serine.

The 8.5 g of N-(3,5-di-t-butyl-4-hydroxycinnamyl)serine so obtained, 3.91 ml of N-benzylpiperazine, and 4.7 g of 1-ethyl-3-(3-dimethylaminopropyl)carbodiimide hydrochloride were added to 20 ml of dichloromethane, and the mixture was allowed to react for 3 hours at room temperature. After completion of the reaction, this mixture was washed by addition of water, and then dichloromethane was distilled off under reduced pressure. The residue so obtained was separated and purified by column chromatography on silica gel, using chloroform containing 1% methanol as an eluent, thereby obtaining 2.3 g of the desired Compound 24 (yield 6.2%).

EXAMPLE 11

Synthesis of Compound 26

First, 2.76 g of 3,5-di-t-butyl-4-hydroxycinnamic acid, 1.17 g of N-n-butylethanolamine and 2.1 g of 1-ethyl-3-(3-dimethylaminopropyl)carbodiimide hydrochloride was added to 50 ml of dichloromethane, and the mixture was agitated for 3 hours at room temperature. Then, the reaction mixture was poured into water and extracted with chloroform. The chloroform layer was dehydrated with anhydrous sodium sulfate and the solvent was distilled off under reduced pressure. The residue so obtained was separated and purified by column chromathography on silica gel with chloroform containing 1% methanol, after which hexane was added to the residue and crystallization yielded 1.40 g of the desired Compound 26 in the form of white crystals (yield 37%).

EXAMPLE 12

Synthesis of Compound 27

First, 1.9 g of Compound 26 prepared in Example 12 was dissolved in 50 ml of benzene, 0.6 ml of n-butylisocyanate and one drop of triethylamine were added in the solution, and the mixture was then allowed to react for 16 hours at 70° C. After completion of the reaction, the reaction mixture was cooled and concentrated under reduced pressure. The concentrate so obtained was subjected to column chromathography using silica gel as a carrier, eluted with chloroform, the fraction containing the desired compound was collected, and the solvent was distilled off. Then, a mixed solvent of ethyl acetate and hexane was added to the residue and 1.0 g of the desired Compound 27 was obtained by crystallization (yield 42%).

EXAMPLE 13

Synthesis of Compound 28

First, 2.6 g of Compound 26 was dissolved in 30 ml of pyridine, then 1.2 g of Nicotinoyl chloride hydrochloride was added by small portions while conducting a reaction for 10 minutes at room temperature, after which the reaction was continued for 3 hours at 80° C. After completion of the reaction and cooling, 100 ml of chloroform was added, and the mixture so obtained was poured into 100 ml of cold water, which was then extracted three times with 50 ml of chloroform. The organic layers were combined and concentrated under reduced pressure, after which the concentrate was subjected to column chromatography on silica gel and eluted with chloroform. The fraction containing the desired compound was collected and the solvent was distilled off, thereby obtaining 2.2 g of the desired Compound 28 (yield 67%).

EXAMPLE 14

Synthesis of Compound 30

First, 4.0 g of 3,5-di-t-butyl-4-hydroxycinnamic acid, 2.4 g of N-(2-methoxyethyl)benzylamine and 3.4 g of 1-ethyl-3-(3-dimethylaminopropyl)carbodiimide hydrochloride was added to 50 ml of dichloromethane and the mixture so obtained was allowed to react for 2 hours at room temperature. Then, the reaction mixture was washed with water and the solvent was distilled off under reduced pressure. The residue so obtained was subjected to column chromathography on silica gel using chloroform as an eluent, the fraction containing the desired compound was collected, and the solvent was distilled off. A mixed solvent of benzene and hexane was added to the residue, and 4.9 g of the desired Compound 30 was obtained (yield 79.8%).

EXAMPLE 15

Synthesis of Compound 31

First, 3.0 g of 3,5-di-t-butyl-4-hydroxycinnamic acid and 0.84 g of 2-aminoethanethiol were dissolved in 50 ml of dichloromethane, 2.2 g of 1-ethyl-3-(3-dimethylaminopropyl)carbodiimide hydrochloride was added to the solution so obtained and the mixture was allowed to react for 2 hours at room temperature. After completion of the reaction, the reaction mixture was washed with 20 ml of water and evaporated to dryness. The residue so obtained was subjected to column chromathography using silica gel as a carrier, eluted with chloroform, the fraction containing the desired compound was collected, and the solvent was distilled off. Then, the mixed solvent of benzen and n-hexane was added to the residue and 0.6 g of the desired Compound 31 was obtained by crystallization (yield 16%).

EXAMPLE 16

Synthesis of Compound 33

First, 3.0 g of 3,5-di-t-butyl-4-hydroxycinnamic acid, 1.67 g of 2-(4-pyridylthio)ethylamine hydrochloride, 2.2 g of 1-ethyl-3-(3-dimethylaminopropyl)carbodiimide hydrochloride and 1.5 ml of triethylamine were added to 50 ml of dichlromethane and the mixture so obtained was then allowed to react for 2 hours at room temperature. After completion of the reaction, the reaction mixture was washed with water and dichloromethane was distilled off under reduced pressure. The residue was separated and purified by column chromathography on silica gel using chloroformmethanol (9:1) mixture as an eluent, thereby obtaining 1.78 g of the desired Compound 33 (yield 39.6%).

EXAMPLE 17

Synthesis of Compound 34

First, 1.4 g of 3,5-di-t-butyl-4-hydroxycinnamic acid, 0.8 g of 2-phenylthioethylamine, 1.1 g of 1-ethyl-3-(3-dimethylaminopropyl)carbodiimide hydrochloride and 0.7 ml of triethylamine were added to 50 ml of dichloromethane and the mixture so obtained was then allowed to react for 2 hours at room temperature. After completion of the reaction, the reaction mixture was washed by addition of water and dichloromethane was distilled off under reduced pressure. The residue so obtained was separated and purified by column chromathography on silica gel using chloroform as an eluent, thereby obtaining 1.2 g of the desired Compound 34 (yield 56.1%).

EXAMPLE 18

Synthesis of Compound 36

First, 0.50 g of 2-(2-aminoethyl)mercaptobenzimidazole, 0.72 g of 3,5-di-t-butyl-4-hydroxycinnamic acid, and 0.67 g of 1-ethyl-3-(3-dimethylaminopropyl)-carbodiimide hydrochloride were added to 15 ml of dichloromethane and the mixture so obtained was then allowed to react for 2 hours at room temperature. After completion of the reaction, the reaction mixture was washed by addition of water and dichloromethane was distilled off under reduced pressure. The residue so obtained was separated and purified by column chromathography on silica gel using chloroform containing 1% methanol as an eluent, thereby obtaining 0.3 g of the desired Compound 36 (yield 25.6%).

EXAMPLE 19

Synthesis of Compound 38

First, 5.53 g of 3,5-di-t-butyl-4-hydroxycinnamic acid, 4.4 g of N-ethoxycarbonylmethylthioethyl-n-butylamine, and 4.0 g of 1-ethyl-3-(3dimethylaminopropyl)carbodiimide hydrochloride (WSC) were added to 100 ml of dichloromethane and the mixture was agitated for 3 hours at room temperature. Then, this reaction mixture was poured into water, and after chloroform extraction the chloroform layer was dehydrated with anhydrous sodium sulfate and the solvent was distilled off under reduced pressure. The residue so obtained was separated and purified by column chromatography on silica gel with chloroform, after which hexane was added and crystallization yielded 7.34 g of an N-ethoxycarbonylmethylthioethyl-N-n-butylcinnamamide derivative (yield 79.5%) in the form of white crystals.

Then, 4.62 g of the cinnamamide derivative so obtained were dissolved in 70 ml of methanol, and 30 ml of a 1N sodium hydroxide solution was gradually added under ice cooling while stirring over a period of 1 hour. The reaction solution was then restored to room temperature and stirring was further continued for 1 hour. Next, the pH of this solution was adjusted to a value below 3 by addition of 1N hydrochloric acid, and the solution was extracted with chloroform several times. The chloroform layers were combined and dehydrated with anhydrous sodium sulfate, after which the solvent was distilled off under reduced pressure. The residue so obtained was separated and purified by column chromatography on silica gel column with chloroform containing 5% methanol, thereby obtaining 4.16 g of N-carboxymethylthioethyl-N-n-butylcinnamamide derivative in an oily form (yield 92.5%).

Then, 1.05 g of the aforementioned N-carboxymethylcinnamamide derivative obtained above together with 0.25 g of 2-aminothiazole and 0.5 g of WSC was added to 50 ml of dichloromethane and the mixture was stirred for 5 hours at room temperature. Then, this reaction solution was poured into water and extracted with chloroform several times. The chloroform layers were combined and dehydrated with anhydrous sodium sulfate, after which the solvent was distilled off under reduced pressure. The residue so obtained was separated and purified by column chromatography on silica gel with chloroform, thereby obtaining 1.05 g of Compound 38 in the form of an amorphous powder (yield 85%).

EXAMPLE 20

Synthesis of Compound 39

First, 2.76 g of 3,5-di-t-butyl-4-hydroxycinnamic acid, 2.11 g of 2-(n-butylaminoethylthio)pyrimidine and 2.0 g of 1-ethyl-3-(3-dimethylaminopropyl)carbodiimide hydrochloride were added to 50 ml of dichloromethane and the mixture was agitated for 5 hours at room temperature. Then, this mixture was poured into water and extracted with chloroform. The chloroform layer was dehydrated with anhydrous sodium sulfate and the solvent was distilled off under reduced pressure. The residue so obtained was separated and purified by silica gel column chromathography with chloroform, thereby obtaining 3.68 g of the desired Compound 39 in an oily form (yield 79%).

EXAMPLE 21

Synthesis of Compound 40

First, 2.5 g of 3,5-di-t-butyl-4-hydroxycinnamic acid and 2.1 g of ethyl-4-(2-aminoethylamino)benzoate were dissolved in 50 ml of dichloromethane. Then, 1.9 g of 1-ethyl-3-(3-dimethylaminopropyl)carbodiimide hydrochloride was added to the solution obtained above and the mixture was allowed to react for 2 hours at room temperature. After completion of the reaction, the reaction mixture was washed with water and dichloromethane was distilled off under reduced pressure. The residue so obtained was separated and purified by column chromathography on silica gel using chloroform as an eluent, thereby obtaining 3.1 g of the desired Compound 40 (yield 66.4%).

EXAMPLE 22

Synthesis of Compound 43

First, 8.1 g of 3,5-di-t-butyl-4-hydroxycinnamic acid, 7.7 g of ethyl-4-[2-(butylamino)ethylamino]benzoate and 6.0 g of 1-ethyl-3-(3-dimethylaminopropyl)carbodiimide hydrochloride were added to 100 ml of dichloromethane and the mixture so obtained was allowed to react for 2 hours at room temperature. Then, the reaction mixture was washed with water and dichloromethane was distilled off. The residue so obtained was subjected to column chromathography on silica gel using chloroform as an eluent, the fraction containing the desired compound was collected, and the solvent was distilled off. A mixed solvent of benzene and hexane was added to the residue and 9.7 g of the desired Compound 43 was obtained by crystallization (yield 63.8%).

EXAMPLE 23

Synthesis of Compound 44

First, 0.6 g of 3,5-di-t-butyl-4-hydroxycinnamic acid, 0.5 g of N-(2-benzylaminoethyl)nicotinamide and 0.5 g of 1-ethyl-3-(3-dimethylaminopropyl)carbodiimide hydrochloride were added to 20 ml of dichloromethane and the mixture so obtained was allowed to react for 3 hours at room temperature. Then, the reaction mixture was washed with water and dichloromethane was distilled off under reduced pressure. The residue so obtained was subjected to column chromathography on silica gel using chloroform as an eluent, the fraction containing the desired compound was collected, and the solvent was distilled off. Ethyl acetate was added to the residue and 0.55 g of the desired Compound 44 was obtained by crystallization (yield 56.1%).

EXAMPLE 24

Synthesis of Compound 46

First, 7.0 g of 3,5-di-t-butyl-4-hydroxycinnamic acid, 3.0 g of N-butylphenylglycinol were dissolved in 100 ml of dichloromethane. Then, 5.4 g of 1-ethyl-3-(3-dimethylaminopropyl)carbodiimide hydrochloride was added to the solution obtained above and the mixture was allowed to react for 2 hours at room temperature. After completion of the reaction, the reaction mixture was washed twice with 50 ml of water and concentrated under reduced pressure. The concentrate was subjected to column chromathography using silica gel as a carrier, eluted with chloroform, the fraction containing the desired compound was collected, and the solvent was distilled off, thereby obtaining 3.8 g of the desired Compound 46 (yield 34%).

EXAMPLE 25

Synthesis of Compound 48

First, 1.4 g of 3,5-di-t-butyl-4-hydroxycinnamic acid, 0.64 ml of 1-phenylethylamine and 1.2 g of 1-ethyl-3-(3-dimethylaminopropyl)carbodiimide hydrochloride were dissolved in 30 ml of dichloromethane and the solution was then allowed to react for 2 hours at room temperature. After completion of the reaction, the reaction mixture was washed with water and dichloromethane was distilled off under reduced pressure. The residue was subjected to column chromathography using silica gel as a carrier, eluted with chloroform, the fraction containing the desired compound was collected, and the solvent was distilled off. A mixed solvent of ethyl acetate and n-hexane was added to the residue and 1.4 g of the desired Compound 48 was obtained by crystallization (yield 73.7%).

EXAMPLE 26

Synthesis of Compound 51

First, 3.6 g of 3,5-di-t-butyl-4-hydroxycinnamic acid and 4.4 g of N-4-(4-benzyl-1-piperazinyl)benzylbutylamine were dissolved in 50 ml of dichloromethane. Then, 3.0 g of 1-ethyl-3-(3-dimethylaminopropyl)carbodiimide hydrochloride was added to the solution obtained above and the mixture was allowed to react for 2 hours at room temperature. The reaction mixture was washed twice with 50 ml of water and concentrated under reduced pressure. The concentrate was subjected to column chromathography using silica gel as a carrier, eluted with chloroform, the fraction containing the desired compound was collected, and the solvent was distilled off, thereby obtaining 6.3 g of the desired Compound 51 (yield 82%).

EXAMPLE 27

Synthesis of Compound 53

First, 13.8 g of 3,5-di-t-butyl-4-hydroxycinnamic acid, 10.9 g of ethyl N-butyl-p-aminobenzoate and 11.0 g of 1-ethyl-3-(3-dimethylaminopropyl)carbodiimide hydrochloride were added to 300 ml of dichloromethane and the mixture was allowed to react for 3 hours at room temperature. This reaction solution was then washed with water and concentrated under reduced pressure. The concentrate so obtained was chromatographed on a silica gel column with chloroform as an eluent, the fraction containing the desired compound was collected and the solvent was distilled off. Then, a mixed solvent of ethyl acetate and hexane was added to the residue so obtained and 9.4 g of N-butyl-N-p-ethoxycarbonylphenyl-3,5-di-t-butyl-4-hydroxycinnamamide was obtained by crystallization (yield 39.2%).

Then, 6.0 g of the aforementioned N-butyl-N-p-ethoxycarbonylphenyl-3,5-di-t-butyl-4-hydroxycinnamamide so obtained was dissolved in 20 ml of ethanol, 25 ml of 2N sodium hydroxide was added to the solution, and a saponification reaction was conducted for 4 hours at 80° C. After completion of the reaction, this reaction solution was acidified by addition of 2N hydrochloric acid, after which the solution was extracted with chloroform several times. The chloroform layers were combined and concentrated, then benzene was added and 3.1 g of N-butyl-N-p-carboxyphenyl-3,5-di-t-butyl-4-hydroxycinnamamide was obtained by crystallization (yield 55.4%).

Next, 1.6 g of the N-butyl-N-p-carboxyphenyl-3,5-di-t-butyl-4-hydroxycinnamamide so obtained together with 0.5 ml of 2-aminomethyl-1-ethylpyrrolidine and 0.8 g of 1-ethyl-3-(3-dimethylaminopropyl)carbodiimide hydrochloride was added to 20 ml of dichloromethane, and the mixture was allowed to react for 2 hours at room temperature. This reaction solution was then washed with water and the dichloromethane was distilled off. The residue so obtained was subjected to column chromatography on silica gel using chloroform as an eluent, the fraction containing the desired compound was collected and the solvent was distilled off. Then, a mixed ethyl acetate-hexane solvent was added to the residue so obtained and 0.94 g of the desired Compound 53 was obtained by crystallization (yield 47.0%).

EXAMPLE 28

Synthesis of Compound 55

First, 7.5 g of 3,5-di-t-butyl-4-hydroxycinnamic acid, 6.4 g of N-butyl-p-ethoxycarbonylbenzylamine and 5.7 g of 1-ethyl-3-(3-dimethylaminopropyl)carbodiimide hydrochloride were added to 100 ml of dichloromethane, and the mixture was allowed to react for 2 hours at room temperature. This reaction solution was washed with water and the dichloromethane was distilled off. Then, 100 ml of 10% sodium hydroxide and 50 ml of ethanol were added to the residue so obtained, and the mixture was allowed to react for 16 hours at room temperature. After completion of the reaction, this reaction solution was acidified by addition of 2N hydrochloric acid and the mixture was extracted with chloroform several times. The chloroform layers were combined, the solvent was distilled off, and the residue so obtained was subjected to column chromatography on silica gel using chloroform containing 5% methanol as an eluent. The fraction containing the desired compound was collected and the solvent was removed by distillation, after which benzene was added to the residue so obtained and 7.6 g of N-butyl-N-p-carboxybenzyl-3,5-di-t-butyl-4-hydroxycinnamamide was obtained by crystallization (yield 60.6%).

Then, 3.3 g of the N-butyl-N-p-carboxybenzyl-3,5-di-t-butyl-4-hydroxycinnamamide obtained above, together with 0.7 g of 2-aminothiazole and 1.9 g of 1-ethyl-3-(3-dimethylaminopropyl)carbodiimide hydrochloride, was added to 50 ml of dichloromethane, and the solution was allowed to react for 2 hours at room temperature. This reaction solution was washed with water and the dichloromethane was removed by distillation. Then, the residue so obtained was subjected to silica gel column chromatography using chloroform as an eluent, the fraction containing the desired compound was collected and the solvent was removed by distillation, after which benzene was added to the residue so obtained and 1.9 g of the desired Compound 55 was obtained by crystallization (yield 50.0%).

EXAMPLE 29

Synthesis of Compound 57

First, 2.8 g of 3,5-di-t-butyl-4-hydroxycinnamic acid, and 1.1 ml of benzylamine were dissolved in 50 ml of dichloromethane. Then, 2.1 g of 1-ethyl-3-(3-dimethylaminopropyl)carbodiimide hydrochloride was added to the solution obtained above and the mixture was allowed to react for 2 hours at room temperature. After completion of the reaction, the reaction mixture was washed twice with water and concentrated under reduced pressure. The concentrate was subjected to column chromathography using silica gel as a carrier, eluted with chloroform, the fraction containing the desired compound was collected, and the solvent was distilled off. A mixed solvent of ethyl acetate and hexane was added to the residue, and 2.4 g of the desired Compound 57 was obtained by crystallization (yield 66%).

EXAMPLE 30

Synthesis of Compound 61

First, 2.2 g of 3,5-di-t-butyl-4-hydroxycinnamic acid, and 1.0 g of 3-fluorobenzylamine were dissolved in 50 ml of dichloromethane. Then, 2.0 g of 1-ethyl-3-(3-dimethylaminopropyl)carbodiimide hydrochloride was added to the solution obtained above and the mixture was allowed to react for 2 hours at room temperature. After completion of the reaction, the reaction mixture was washed twice with 50 ml of water and the solvent was distilled off under reduced pressure. The residue was subjected to column chromathography using silica gel as a carrier, eluted with chloroform, the fraction containing the desired compound was collected, and the solvent was distilled off. A mixed solvent of ethyl acetate and hexane was added to the residue and 1.7 g of the desired Compound 61 was obtained by crystallization (yield 55%).

EXAMPLE 31

Synthesis of Compound 62

First, 2.8 g of 3,5-di-t-butyl-4-hydroxycinnamic acid was dissolved in 50 ml of dichloromethane, then 3.6 ml of thionyl chloride was added, and the mixture was heated and refluxed for 1 hour. The reaction mixture was then left to cool, and then concentrated under reduced pressure. 50 ml of chloroform was added to the concentrate so obtained, and this was dripped under ice cooling into a solution prepared by dissolving 1.5 g of 4-(aminomethyl)benzoic acid in a mixture of 10 ml of pyridine and 30 ml of chloroform. After the dripping operation was completed, the mixture was heated and refluxed for 1 hour. This reaction solution was then poured into 50 ml of water, after which the mixture was extracted with 50 ml of chloroform three times. The chloroform layers were combined and the solvent was distilled off under reduced pressure. Then, the residue was subjected to column chromatography using silica gel as a carrier, and eluted with chloroform containing 5% methanol. The fraction containing the desired compound was collected, and the solvent was distilled off. Dichloromethane was added to the residue so obtained, and 0.9 g of the desired Compound 62 was obtained by crystallization (yield 22%).

EXAMPLE 32

Synthesis of Compound 65

First, 2.8 g of 3,5-di-t-butyl-4-hydroxycinnamic acid and 1.2 ml of 2-(aminoethyl)pyridine were dissolved in 50 ml of dichloromethane. Then, 2.1 g of 1-ethyl-3-(3-dimethylaminopropyl)carbodiimide hydrochloride was added to the solution obtained above and the mixture was allowed to react for 2 hours at room temperature. After completion of the reaction, the reaction mixture was washed twice with 50 ml of water and concentrated under reduced pressure. The concentrate was subjected to column chromathography using silica gel as a carrier, eluted with chloroform, the fraction containing the desired compound was collected, and the solvent was distilled off. Ethyl acetate was added to the residue and 2.2 g of the desired Compound 65 was obtained by crystallization (yield 58%).

EXAMPLE 33

Synthesis of Compound 66

First, 3.0 g of 3,5-di-t-butyl-4-hydroxycinnamic acid, and 1.3 ml of 1-(3-aminopropyl)imidazole were dissolved in 50 ml of dichloromethane. Then, 2.2 g of 1-ethyl-3-(3-dimethylaminopropyl)carbodiimide hydrochloride was added to the solution obtained above and the mixture was allowed to react for 2 hours at room temperature. After completion of the reaction, the reaction mixture was washed with 20 ml of water and evaporated to dryness The residue was subjected to column chromathography using silica gel as a carrier, eluted with chloroform containing 1% methanol, the fraction containing the desired compound was collected, and the solvent was distilled off. A mixed solvent of ethyl acetate and hexane was added to the residue and 2.4 g of the desired Compound 66 was obtained by crystallization (yield 58%).

EXAMPLE 34

Synthesis of Compound 75

First, 1.38 g of 3,5-di-t-butyl-4-hydroxycinnamic acid, 1.0 g of 3-(n-butylaminomethyl)indole and 1.0 g of 1-ethyl-3-(3-dimethylaminopropyl)carbodiimide hydrochloride was added to 50 ml of dichloromethane and the mixture so obtained was agitated for 3 hours at room temperature. Then, the reaction mixture was poured into water and extracted with chloroform. The chloroform layer was dehydrated with anhydrous sodium sulfate and the solvent was distilled off under reduced pressure. The residue so obtained was separated and purified by silica gel column chromatography with chloroform, thereby obtaining 0.65 g of the desired Compound 75 in the form of an amorphous powder (yield 28.1%).

EXAMPLE 35

Synthesis of Compound 77

First, 2.76 g of 3,5-di-t-butyl-4-hydroxycinnamic acid, 1.98 g of 4-(benzylaminomethyl)pyridine and 2.0 g of 1-ethyl-3-(3-dimethylaminopropyl)carbodiimide hydrochloride was added to 50 ml of dichloromethane and the mixture so obtained was agitated for 3 hours at room temperature. Then, the reaction mixture was poured into water and extracted with chloroform. The chloroform layer was dehydrated with anhydrous sodium sulfate and the solvent was distilled off under reduced pressure. The residue so obtained was separated and purified by silica gel column chromathography with chloroform and then with chloroform containing 2% methanol, after which hexane was added and crystallization yielded 2.71 g of the desired Compound 77 in the form of white crystals (yield 59%).

EXAMPLE 36

Synthesis of Compound 79

First, 5.6 g of 3,5-di-t-butyl-4-hydroxycinnamic acid, 5.3 g of 1-[2-(butylamino)ethyl]-4-(2-pyridyl)piperazine and 4.0 g of 1-ethyl-3-(3-dimethylaminopropyl)carbodiimide hydrochloride was added to 50 ml of dichloromethane and the mixture so obtained was allowed to react for 3 hours at room temperature. Then, the reaction mixture was washed with water and dichloromethane was distilled off. The residue so obtained was subjected to column chromathography on silica gel using chloroform as an eluent, the fraction containing the desired compound was collected, and the solvent was distilled off. A mixed solvent of ethyl acetate and hexane was added to the residue and 6.1 g of the desired Compound 79 was obtained by crystallization (yield 58.7%).

EXAMPLE 37

Synthesis or Compound 80

First, 3.5 g of 3,5-di-t-butyl-4-hydroxycinnamic acid and 1.5 g of 2-aminoisobutyric acid methyl ester hydrochloride was suspended in 50 ml of dichloromethane. Then, 2.4 g of 1-ethyl-3-(3-dimethylaminopropyl)carbodiimide hydrochloride and 1.8 ml of triethylamine were added to the suspension obtained above and the mixture was allowed to react for 2 hours at room temperature. After completion of the reaction, the reaction mixture was washed with 20 ml of water and evaporated to dryness. The residue was subjected to column chromatography using silica gel as a carrier, eluted with chloroform, the fraction containing the desired compound was collected, and the solvent was distilled off. A mixed solvent of benzene and n-hexane was added to the residue and 1.24 g of the desired Compound 80 was obtained by crystallization (yield 26%).

EXAMPLE 38

Synthesis of Compound 81

First, 1.52 g of 3,5-di-t-butyl-4-hydroxycinnamic acid, 1 g of (±)-α-amino-γ-butyrolactone hydrobromide and 1.16 g of 1-ethyl-3-(3-dimethylaminopropyl)-carbodiimide hydrochloride were added to 50 ml of dichloromethane and the mixture so obtained was agitated for 18 hours at room temperature. Then, the mixture was washed with water, the organic layer was dehydrated with anhydrous sodium carbonate, and the solvent was distilled off under reduced pressure. The oily substance so obtained was separated and purified by silica gel column chromathography with chloroform containing 2% methanol, after which recrystallization from ligroin yielded 1.1 g of the desired Compound 81 in the form of white crystals (yield 56%).

EXAMPLE 39

Synthesis of Compound 83

First, 2.76 g of 3,5-di-t-butyl-4-hydroxycinnamic acid and 1.7 g of 2-aminoindan hydrochloride were dissolved in 50 ml of dichloromethane. Then, 2.0 g of 1-ethyl-3-(3-dimethylaminopropyl)carbodiimide hydrochloride and 1.4 ml of triethylamine were added to the solution obtained above and the mixture was allowed to react for 5 hours at room temperature. To the reaction mixture, water was added and the mixture was extracted with chloroform several times. The organic layers were combined, first washed with dilute hydrochloric acid, and then with water, and evaporated to dryness under reduced pressure. The residue so obtained was subjected to column chromathography using silica gel as a carrier, eluted with chloroform, the fraction containing the desired compound was collected, and the solvent was distilled off. A mixed solvent of ethyl acetate and n-hexane was added to the residue and 3.46 g of the desired Compound 83 was obtained by crystallization (yield 89%).

EXAMPLE 40

Synthesis of Compound 86

First, 2.2 g of 3,5-di-t-butyl-4-hydroxycinnamic acid was dissolved in 10 ml of THF and this solution was added to the mixture of 1.91 g of piperidine and 10 ml of THF under ice cooling. Then, the mixture so obtained was agitated for 4 hours. To this mixture, 100 ml of ether was added and the mixture was washed twice with water. The organic layer was dehydrated with sodium sulfate and then evaporated to dryness. The residue was recrystallized from benzene, thereby obtaining 700 mg of the desired Compound 86.

EXAMPLE 41

Synthesis of Compound 89

First, 2.76 g of 3,5-di-t-butyl-4-hydroxycinnamic acid and 1.57 g of ethyl pipecolinate were dissolved in 70 ml of dichloromethane. Then, 2.1 g of 1-ethyl-3-(3-dimethylaminopropyl)carbodiimide hydrochloride was added to the solution obtained above and the mixture was allowed to react for 5 hours at room temperature. After completion of the reaction, the reaction mixture was washed with water and evaporated to dryness under reduced pressure. To the residue, ethyl acetate was added, and 3.3 g of the desired Compound 89 was obtained by crystallization (yield 80%).

EXAMPLE 42

Synthesis of Compound 92

First, 2.76 g of 3,5-di-t-butyl-4-hydroxycinnamic acid and 1.71 g of N-benzylpiperazine were dissolved in 70 ml of dichloromethane. Then, 2.1 g of 1-ethyl-3-(3-dimethylaminopropyl)carbodiimide hydrochloride was added to the solution obtained above and the mixture was allowed to react for 3 hours at room temperature. After completion of the reaction, the reaction mixture was washed with water and evaporated to dryness under reduced pressure To the residue, ethyl acetate was added and 3.1 g of the desired Compound 92 was obtained by crystallization (yield 2%).

EXAMPLE 43

Synthesis of Compound 93

First, 2.76 g of 3,5-di-t-butyl-4-hydroxycinnamic acid and 1.63 g of N-(α-pyridyl)piperazine were dissolved in 70 ml of dichloromethane. Then, 2.1 g of 1-ethyl-3-(3-dimethylaminopropyl)carbodiimide hydrochloride was added to the solution obtained above and the mixture was allowed to react for 3 hours at room temperature. After completion of the reaction, the reaction mixture was washed with water and evaporated to dryness under reduced pressure. Ethyl acetate was added to the residue so obtained, and 3.0 g of the desired Compound 93 was obtained by crystallization (yield 71%).

EXAMPLE 44

First, 100 g of Compound 3, 55 g of lactose and 41 g of dry potato starch were kneaded together with 20 ml of water, then the mixture was pressed through a 16-mesh screen and dried at 40° C., resulting in granules. Then, the granules were uniformly mixed with 4 g of magnesium stearate and compressed by the conventional method, thereby obtaining tablets. The weight of each tablet was 200 mg and each tablet contained 100 mg of Compound 3.

EXAMPLE 45

Using Compound 57 in place of Compound 3, tablets were prepared by the same procedure as in EXAMPLE 44. The weight of each tablet was 200 mg and each tablet contained 100 mg of Compound 57.

EXAMPLE 46

Using Compound 61 in place of Compound 3, tablets were prepared by the same procedure as in Example 44. The weight of each tablet was 200 mg and each tablet contained 100 mg of Compound 61.

EXAMPLE 47

First, 196 g of the granules obtained by the same procedure as in Example 44 was mixed with 4 g of magnesium stearate. Then, hard capsules (No. 2) were charged with 200 mg aliquots of this mixture. Each of the resulting hard capsulated preparations contained 100 mg of Compound 3.

EXAMPLE 48

Using Compound 57 in place of Compound 3, hard capsulated preparations were prepared by the same procedure as in Example 47. Each of the resulting hard capsulated preparations contained 100 mg of Compound 57.

EXAMPLE 49

Using Compound 61 in place of Compound 3, hard capsulated preparations were prepared by the same procedure as in Example 47. Each of the resulting hard capsulated preparations contained 100 mg of Compound 61.

EXAMPLE 50

| | |
|---|---|
| Compound 3 | 10.0 g |
| Lactose | 85.0 g |
| Crystalline cellulose | 4.5 g |
| Magnesium stearate | 1.5 g |

The aforementioned ingredients were thoroughly mixed, thereby obtaining a powder containing 100 mg of Compound 3 per gram.

EXAMPLE 51

Using Compound 57 in place of Compound 3, a powder containing 100 mg of Compound 57 per gram was obtained by the same procedure as in Example 50.

EXAMPLE 52

Using Compound 61 in place of Compound 3, a powder containing 100 mg of Compound 61 per gram was obtained by the same procedure as in Example 50.

Experiment 1

Antihyperlipidemic effects of Compounds 1-93

Table 1, prepared by the methods of Examples 1-43 or by similar methods, were evaluated in accordance with the following protocol using Wistar rats.

Male Wistar rats (mean body weight 150 g) were divided into groups for this experiment, each groups including six rats. The Wistar rats in each group were fed ad libitum for 7 days a diet containing Chow CA-1 (supplied by Clea Japan, Inc.) supplemented with 1.5% cholesterol, 0.5% cholic acid and 5% olive oil. Test compounds were suspended in a 2.5% (w/v) gum arabic solution and administered orally to the rats on the 4th, 5th, 6th and 7th days in a volume of 3 ml/kg body weight.

After the final administration of the compounds, the animals were fasted overnight, and on the 8th day blood was taken from the inferior vena cava under ether anesthesia, and the serum was obtained by centrifugation.

Serum levels of total cholesterol (T-C) and HDL-cholesterol (HDL-C) were measured by enzymatic methods with a TC Kit-K (Nippon Shoji Kaisha, LTD.) and a HDL-C Kit-N (Nippon Shoji Kaisha LTD.), respectively. The serum levels were also determined for the control group which received only an aqueous gum arabic solution. The rate of change for each serum levels was calculated by the following formula.

$$\text{Rate of change (\%)} = \frac{\text{(Value for group treated with tested compound)} - \text{(Value for control group)}}{\text{Value for control group}} \times 100$$

The difference between the values of T-C and HDL-C were calculated, and this difference was regarded as the sum of the levels of VLDL- (very low density lipoprotein) and LDL-cholesterol. The rate of change for the sum of the levels of VLDL- and LDL-cholesterol was also calculated. The results are shown in Table 2. These results demonstrate that the cinnamamide derivatives of the present invention display excellent antihyperlipidemic efficacy.

TABLE 2

| Compound No. | Dosage (mg/kg/day) | T—C | HDL—C | (T—C) − (HDL—C) |
|---|---|---|---|---|
| 1 | 25 | −12 | 30 | −25 |
| 2 | 50 | −17 | 25 | −29 |
| 3 | 10 | −30 | 61 | −58 |
| 4 | 50 | −10 | 20 | −11 |
| 5 | 50 | −30 | 42 | −49 |
| 6 | 50 | −30 | 10 | −36 |
| 7 | 50 | −33 | 23 | −54 |
| 8 | 50 | −10 | 22 | −21 |
| 9 | 50 | −20 | 92 | −48 |
| 10 | 50 | −28 | 37 | −45 |
| 11 | 10 | −34 | 25 | −45 |
| 12 | 25 | −43 | 34 | −58 |
| 14 | 50 | −35 | 10 | −45 |
| 15 | 50 | −43 | 48 | −66 |
| 16 | 25 | −32 | 114 | −77 |
| 17 | 25 | −19 | 33 | −35 |
| 18 | 50 | −36 | 13 | −53 |
| 19 | 50 | −37 | 15 | −50 |
| 20 | 50 | −45 | 17 | −55 |
| 22 | 25 | −18 | 114 | −67 |
| 23 | 25 | −36 | 119 | −84 |
| 24 | 50 | −47 | 14 | −60 |
| 25 | 25 | −17 | 23 | −31 |
| 26 | 25 | −37 | 108 | −82 |
| 27 | 25 | −29 | 39 | −48 |
| 28 | 25 | −35 | 95 | −82 |
| 29 | 50 | −44 | 126 | −82 |
| 30 | 50 | −42 | 69 | −67 |
| 31 | 50 | −31 | 55 | −54 |
| 32 | 50 | −38 | 63 | −63 |
| 33 | 25 | −31 | 75 | −63 |
| 34 | 25 | −40 | 116 | −86 |
| 35 | 50 | −22 | 15 | −37 |
| 36 | 50 | −10 | 207 | −66 |
| 37 | 50 | −23 | 50 | −40 |
| 38 | 25 | −37 | 33 | −63 |
| 39 | 25 | −22 | 39 | −41 |
| 40 | 50 | −31 | 44 | −49 |
| 41 | 50 | −15 | 27 | −32 |
| 42 | 50 | −32 | 10 | −40 |
| 43 | 50 | −47 | 12 | −56 |
| 44 | 50 | −35 | 11 | −43 |
| 45 | 25 | −26 | 76 | −55 |
| 46 | 25 | −14 | 15 | −21 |
| 47 | 50 | −27 | 96 | −55 |
| 48 | 50 | −40 | 139 | −81 |
| 49 | 50 | −57 | 43 | −79 |
| 50 | 50 | −46 | 13 | −58 |
| 51 | 50 | −29 | 80 | −53 |
| 52 | 50 | −38 | 10 | −47 |
| 53 | 50 | −44 | 10 | −50 |
| 54 | 50 | −14 | 13 | −17 |
| 55 | 50 | −11 | 175 | −17 |
| 56 | 50 | −14 | 70 | −36 |
| 57 | 10 | −30 | 153 | −77 |
| 58 | 10 | −18 | 76 | −51 |
| 59 | 10 | −24 | 72 | −54 |
| 60 | 10 | −24 | 54 | −48 |
| 61 | 10 | −29 | 126 | −77 |
| 62 | 50 | −22 | 93 | −56 |
| 63 | 50 | −35 | 56 | −59 |
| 64 | 25 | −42 | 36 | −70 |
| 65 | 25 | −38 | 38 | −62 |
| 66 | 50 | −25 | 51 | −45 |
| 67 | 50 | −14 | 65 | −34 |
| 68 | 50 | −40 | 11 | −50 |
| 69 | 25 | −31 | 38 | −50 |
| 70 | 25 | −45 | 29 | −68 |
| 71 | 50 | −17 | 28 | −28 |
| 72 | 25 | −50 | 34 | −81 |
| 73 | 50 | −41 | 11 | −54 |
| 74 | 25 | −30 | 73 | −68 |
| 75 | 25 | −14 | 46 | −30 |
| 76 | 25 | −33 | 75 | −61 |
| 77 | 25 | −22 | 51 | −44 |
| 78 | 50 | −26 | 39 | −40 |
| 79 | 50 | −13 | 131 | −45 |
| 80 | 50 | −47 | 13 | −61 |
| 81 | 50 | −15 | 12 | −31 |
| 82 | 50 | −23 | 49 | −51 |
| 83 | 25 | −32 | 157 | −89 |
| 84 | 50 | −11 | 13 | −19 |
| 85 | 50 | −10 | 109 | −24 |
| 86 | 50 | −12 | 34 | −27 |
| 88 | 50 | −22 | 86 | −49 |
| 89 | 50 | −11 | 42 | −37 |

TABLE 2-continued

| Compound No. | Dosage (mg/kg/day) | Rate of change in cholesterol level (%) | | |
|---|---|---|---|---|
| | | T—C | HDL—C | (T—C) − (HDL—C) |
| 90 | 50 | −10 | 11 | −18 |
| 91 | 50 | −15 | 10 | −21 |
| 92 | 10 | −24 | 21 | −38 |
| 93 | 10 | −15 | 39 | −32 |

Experiment 2

Acute toxicity of Compounds 1-93 listed in Table 1 was evaluated using ddY mice in accordance with the following protocol.

Six male ddY mice weighing 27-30 g were used in each group. The compounds 1-93 were suspended in a 0.5% sodium carboxymethylcellulose solution and administered orally to the mice in a volume of 0.1 ml/10 g body weight. For two weeks after the administration, general symptoms in the animals were observed and deaths were checked. None of the compounds 1-93 of the present invention induced deaths even when administered at a dose of 500 mg/kg. As the results show, the values of LD50 (50% lethal dose) for compounds 1-93 were estimated to be greater than 500 mg/kg indicating very low toxicity.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A cinnamamide derivative of formula I or the salts thereof:

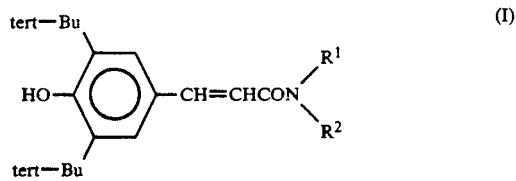

wherein $R^1$ is selected from the group consisting of alkyl having 1 to 8 carbon atoms;

—$(CN_2)_{n^1}COR^3$, wherein $R^3$ is —OH, —$OR^4$ ($R^4$ is alkyl having 1 to 3 carbon atoms, —$NHR^5$ ($R^5$ is alkyl having 1 to 3 carbon atoms), —$NH(CH_2)_{n^2}$—$C_6H_5$ ($n^2$ is an integer of 0 to 3), or —$NHNH$—$C_6H_5$, and $n^1$ is an integer of 1 to 3;

—CHCOR$^9$,
|
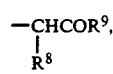

wherein $R^8$ is alkyl having 1 to 5 carbon atoms, —$(CH_2)_{n^4}COOR^{10}$ ($R^{10}$ is hydrogen or alkyl having 1 to 3 carbon atoms, and $n^4$ is an integer of 1 to 3), phenyl or hydroxyphenyl, and $R^9$ is —OH, or —$OR^{11}$ ($R^{11}$ is an alkyl having 1 to 3 carbon atoms);

—$(CH_2)_{n^7}OR^{12}$, wherein $R^{12}$ is hydrogen, alkyl having 1 to 3 carbon atoms, —$CONHR^{13}$ ($R^{13}$ is alkyl having 1 to 5 carbon atoms), or —$COR^{14}$ ($R^{14}$ is phenyl, halogen-substituted phenyl), and $n^7$ is an integer of 1 to 3;

—$(CH_2)_{n^8}SR^{15}$, wherein $R^{15}$ is hydrogen, —$(CH_2)_{n^9}COOR^{17}$ ($R^{17}$ is alkyl having 1 to 3 carbon atoms and $n^9$ is an integer of 0 to 3), or —$(CH_2)_{n^{11}}R^{18}$ ($R^{18}$ is phenyl, and $n^{11}$ is an integer of 0 to 3), and $n^8$ is an integer of 1 to 3;

—$(CH_2)_{n^{12}}NHR^{19}$, wherein $R^{19}$ is

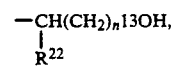

($R^{20}$ is hydrogen or alkyl having 1 to 3 carbon atoms), and $n^{12}$ is an integer of 1 to 3;

—CH$(CH_2)_{n^{13}}$OH,
|
$R^{22}$ wherein $R^{22}$ is phenyl, hydroxyphenyl, and $n^{13}$ is an integer of 1 to 3;

—$(CH_2)_{n^{14}}$CHCH$_2$OH,
|
$R^{23}$ wherein $R^{23}$ is —OH or phenyl, and $n^{14}$ is an integer of 1 to 3;

—CH—C$_6$H$_5$,
|
$R^{24}$ wherein $R^{24}$ is alkyl having 1 to 3 carbon atoms, phenyl, or —CN;

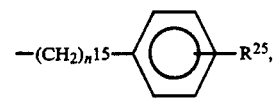

wherein $R^{25}$ is $$-O-\underset{\underset{CH_3}{|}}{\overset{\overset{CH_3}{|}}{C}}-COOH,$$

and $n^{15}$ is an integer of 0 to 3;

—$(CH_2)_{n^{18}}R^{28}$, wherein $R^{28}$ is —CN,

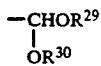

($R^{29}$ and $R^{30}$ are independently alkyl having 1 to 3 carbon atoms),

wherein $R^{31}$ is hydrogen, halogen, $-NO_2$, $-COOH$, $COOR^3$ wherein $R^{33}$ is alkyl containing 1 to 3 carbon atoms, or $-OR^{34}$ wherein $R^{34}$ is alkyl containing 1 to 3 carbon atoms and $R^{32}$ is hydrogen or $OR^{35}$ wherein $R^{35}$ is alkyl containing 1 to 3 carbon atoms,

($R^{36}$ and $R^{37}$ are independently alkyl having 1 to 3 carbon atoms), and $n^{18}$ is an integer of 0 to 3;

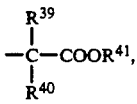

wherein $R^{39}$, $R^{40}$ and $R^{41}$ are independently alkyl having 1 to 3 carbon atoms;

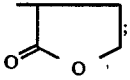

naphthyl;
indanyl;
tetralinyl; and
$-COR^{42}$,
wherein $R^{42}$ is alkyl having 1 to 3 carbon atoms; and
when $R^1$ is an alkyl group, $R^2$ is $-(CH_2)n^{19}-C_6H_5$ ($n^{19}$ is an integer of 1 to 3);
or when $R^1$ is not an alkyl group, $R^2$ is selected from the group consisting of hydrogen, alkyl having 1 to 5 carbon atoms, and $-(CH_2)_n19-C_6H_5$ ($n^{19}$ is an integer of 1 to 3).

2. An antihyperlipidemic composition comprising an active ingredient of a cinnamamide derivative and a pharmaceutically acceptable diluent, wherein said active ingredient is at least one selected from the group consisting of a cinnamamide derivative of claim 1 and the pharmaceutically acceptable salt thereof.

* * * * *